(12) United States Patent
Tulkis et al.

(10) Patent No.: US 8,152,855 B2
(45) Date of Patent: Apr. 10, 2012

(54) METHOD AND APPARATUS FOR HIP FEMORAL RESURFACING TOOLING

(75) Inventors: Peter Tulkis, Paramus, NJ (US); Robert E. Ledger, River Vale, NJ (US); Patrick Raugel, Ramsey, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 12/884,502

(22) Filed: Sep. 17, 2010

(65) Prior Publication Data

US 2011/0004318 A1    Jan. 6, 2011

Related U.S. Application Data

(62) Division of application No. 11/593,168, filed on Nov. 3, 2006, now abandoned.

(51) Int. Cl.
*A61F 2/36* (2006.01)
*A61F 2/32* (2006.01)
*A61F 2/46* (2006.01)
*A61B 17/56* (2006.01)

(52) U.S. Cl. ............... 623/23.12; 623/23.13; 623/22.12; 606/99; 606/89; 606/104

(58) Field of Classification Search .......... 606/86 R–89, 606/96–100, 104; 623/22.11–22.2, 23.11–23.14
See application file for complete search history.

(56) References Cited

U.S. PATENT DOCUMENTS

| | | | |
|---|---|---|---|
| 2,622,592 A | 12/1952 | Rosenstein | |
| 2,650,588 A | 9/1953 | Drew | |
| 2,668,531 A | 2/1954 | Haboush | |
| 2,685,877 A | 8/1954 | Dobelle | |
| 2,718,228 A | 9/1955 | Van Steenbrugghe | |
| 2,755,865 A | 7/1956 | Jacobs | |
| 2,934,065 A | 4/1960 | Townley | |
| 3,028,183 A | 4/1962 | Phillips | |
| 3,053,251 A | 9/1962 | Black et al. | |
| 3,543,749 A | 12/1970 | Grove | |
| 3,818,514 A | 6/1974 | Clark | |

(Continued)

FOREIGN PATENT DOCUMENTS

AT        413259 T    11/2008

(Continued)

OTHER PUBLICATIONS

BHR Resurfacing Studies, www.midmedtec.com, printed Jun. 24, 2004.

(Continued)

*Primary Examiner* — Thomas C. Barrett
*Assistant Examiner* — Michael T Schaper

(74) *Attorney, Agent, or Firm* — Lerner, David, Littenberg, Krumholz & Mentlik, LLP

(57) ABSTRACT

Tools and methods for implanting hip resurfacing femoral prostheses along a path defined by the axis of a shaped femoral head surface are described. The prostheses are stemless partial ball components having an outer surface shaped to conform to an acetabular socket and may be a two part design having a mating sleeve component with an internal bore adapted to receive the shaped femoral head. The tools and methods are capable of accurately implanting both one and two piece ball components and sleeves without requiring the prosthesis to have a central stem or the preparation of a stem cavity in the femoral head and neck.

8 Claims, 22 Drawing Sheets

U.S. PATENT DOCUMENTS

| | | | |
|---|---|---|---|
| 3,925,824 A | 12/1975 | Freeman et al. | |
| 4,005,495 A | 2/1977 | Locke et al. | |
| 4,007,494 A | 2/1977 | Sauer | |
| 4,035,848 A | 7/1977 | Wagner | |
| 4,123,806 A | 11/1978 | Amstutz et al. | |
| 4,135,517 A | 1/1979 | Reale | |
| 4,173,797 A | 11/1979 | Langlais et al. | |
| 4,224,699 A | 9/1980 | Weber | |
| 4,246,895 A * | 1/1981 | Rehder | 606/89 |
| 4,274,164 A | 6/1981 | Rehder et al. | |
| 4,284,080 A * | 8/1981 | Rehder | 606/80 |
| 4,312,079 A | 1/1982 | Dorre et al. | |
| 4,328,593 A | 5/1982 | Sutter et al. | |
| 4,332,036 A * | 6/1982 | Sutter et al. | 623/23.42 |
| 4,520,511 A | 6/1985 | Gianezio et al. | |
| 4,528,702 A | 7/1985 | Frey | |
| 4,532,660 A | 8/1985 | Field | |
| 4,532,661 A | 8/1985 | Halpern | |
| 4,542,539 A | 9/1985 | Rowe, Jr. et al. | |
| 4,542,825 A * | 9/1985 | Thomas et al. | 206/363 |
| 4,662,888 A | 5/1987 | Field | |
| 4,752,296 A | 6/1988 | Buechel et al. | |
| 4,846,841 A | 7/1989 | Oh | |
| 4,860,735 A | 8/1989 | Davey et al. | |
| 4,865,609 A | 9/1989 | Roche | |
| 4,896,663 A | 1/1990 | Vandewalls | |
| 4,911,720 A | 3/1990 | Collier | |
| 4,976,740 A * | 12/1990 | Kleiner | 623/23.14 |
| 4,995,883 A | 2/1991 | Demane et al. | |
| 5,007,935 A | 4/1991 | Vincent et al. | |
| 5,066,304 A | 11/1991 | Crowninshield et al. | |
| 5,127,920 A | 7/1992 | MacArthur | |
| 5,133,764 A | 7/1992 | Pappas et al. | |
| 5,133,765 A * | 7/1992 | Cuilleron | 606/89 |
| 5,133,769 A | 7/1992 | Wagner et al. | |
| 5,258,033 A | 11/1993 | Lawes et al. | |
| 5,312,409 A | 5/1994 | McLaughlin et al. | |
| 5,358,526 A | 10/1994 | Tornier | |
| 5,507,830 A | 4/1996 | DeMane et al. | |
| 5,520,694 A | 5/1996 | Dance et al. | |
| 5,569,263 A | 10/1996 | Hein | |
| 5,611,353 A | 3/1997 | Dance et al. | |
| 5,653,714 A | 8/1997 | Dietz et al. | |
| 5,690,638 A | 11/1997 | Dance et al. | |
| 5,713,112 A | 2/1998 | Genero et al. | |
| 5,725,593 A | 3/1998 | Caracciolo | |
| 5,735,905 A | 4/1998 | Parr | |
| 5,788,700 A | 8/1998 | Morawa et al. | |
| 5,868,796 A | 2/1999 | Buechel et al. | |
| 5,911,759 A | 6/1999 | Rogala | |
| 5,972,033 A | 10/1999 | Drouin et al. | |
| 6,096,084 A | 8/2000 | Townley | |
| 6,110,179 A | 8/2000 | Flivik et al. | |
| 6,120,510 A | 9/2000 | Albrektsson et al. | |
| 6,120,544 A | 9/2000 | Grundei et al. | |
| 6,129,764 A | 10/2000 | Servidio | |
| 6,156,069 A * | 12/2000 | Amstutz | 623/22.11 |
| 6,165,177 A | 12/2000 | Wilson et al. | |
| 6,190,416 B1 | 2/2001 | Choteau et al. | |
| 6,231,611 B1 * | 5/2001 | Mosseri | 623/22.12 |
| 6,273,915 B1 | 8/2001 | Grimes | |
| 6,322,564 B1 | 11/2001 | Surma | |
| 6,379,390 B1 | 4/2002 | Advani et al. | |
| 6,383,227 B1 | 5/2002 | Baroud et al. | |
| 6,395,005 B1 | 5/2002 | Lovell | |
| 6,464,728 B1 | 10/2002 | Murray | |
| 6,482,237 B2 | 11/2002 | Mosseri | |
| 6,508,841 B2 | 1/2003 | Martin et al. | |
| 6,524,343 B2 | 2/2003 | Storer et al. | |
| 6,585,771 B1 * | 7/2003 | Buttermilch et al. | 623/22.12 |
| 6,589,282 B2 | 7/2003 | Pearl | |
| 6,595,999 B2 * | 7/2003 | Marchione et al. | 606/96 |
| 6,607,561 B2 | 8/2003 | Brannon | |
| 6,616,697 B2 | 9/2003 | Sotereanos | |
| 6,626,948 B2 | 9/2003 | Storer et al. | |
| 6,673,114 B2 | 1/2004 | Hartdegen et al. | |
| 6,676,706 B1 | 1/2004 | Mears et al. | |
| 6,688,798 B2 | 2/2004 | McDevitt | |
| 6,695,850 B2 | 2/2004 | Diaz | |
| 6,706,073 B2 | 3/2004 | Draenert et al. | |
| 6,740,120 B1 | 5/2004 | Grimes | |
| 6,743,235 B2 | 6/2004 | Subba Rao | |
| 6,802,865 B2 | 10/2004 | Biegun et al. | |
| 6,827,720 B2 | 12/2004 | Leali | |
| 6,860,903 B2 | 3/2005 | Mears et al. | |
| 6,869,434 B2 | 3/2005 | Choi | |
| 6,916,325 B2 | 7/2005 | Kana et al. | |
| 6,942,699 B2 | 9/2005 | Stone et al. | |
| 6,953,480 B2 | 10/2005 | Mears et al. | |
| 7,458,990 B2 * | 12/2008 | Chieng | 623/23.12 |
| 7,488,325 B2 * | 2/2009 | Qian | 606/96 |
| 7,699,847 B2 * | 4/2010 | Sheldon et al. | 606/53 |
| 7,918,856 B2 * | 4/2011 | Guelat et al. | 606/80 |
| 2001/0012967 A1 * | 8/2001 | Mosseri | 623/23.12 |
| 2001/0053935 A1 | 12/2001 | Hartdegen et al. | |
| 2002/0022889 A1 | 2/2002 | Chibrac et al. | |
| 2002/0049501 A1 | 4/2002 | Storer et al. | |
| 2002/0072805 A1 | 6/2002 | Sullivan et al. | |
| 2002/0107577 A1 | 8/2002 | Storer et al. | |
| 2002/0193801 A1 | 12/2002 | Marchione et al. | |
| 2002/0193882 A1 | 12/2002 | Koller | |
| 2003/0014123 A1 | 1/2003 | Copf et al. | |
| 2003/0018391 A1 | 1/2003 | Evans | |
| 2003/0040806 A1 | 2/2003 | MacDonald | |
| 2003/0055431 A1 | 3/2003 | Brannon | |
| 2003/0060889 A1 | 3/2003 | Tarabishy | |
| 2003/0060890 A1 | 3/2003 | Tarabishy | |
| 2003/0065399 A1 | 4/2003 | Brannon | |
| 2003/0125810 A1 | 7/2003 | Sullivan et al. | |
| 2003/0130741 A1 | 7/2003 | McMinn | |
| 2003/0153924 A1 | 8/2003 | Kana et al. | |
| 2003/0163202 A1 | 8/2003 | Lakin | |
| 2003/0187514 A1 | 10/2003 | McMinn | |
| 2003/0216742 A1 | 11/2003 | Wetzler et al. | |
| 2003/0220698 A1 | 11/2003 | Mears et al. | |
| 2003/0229357 A1 * | 12/2003 | Dye | 606/99 |
| 2004/0015238 A1 | 1/2004 | Buehler et al. | |
| 2004/0034431 A1 | 2/2004 | Maroney et al. | |
| 2004/0035848 A1 | 2/2004 | Ohashi et al. | |
| 2004/0037618 A1 | 2/2004 | Hermens et al. | |
| 2004/0054373 A1 | 3/2004 | Serra et al. | |
| 2004/0054419 A1 | 3/2004 | Serra et al. | |
| 2004/0059340 A1 | 3/2004 | Serra et al. | |
| 2004/0059429 A1 | 3/2004 | Amin et al. | |
| 2004/0107001 A1 | 6/2004 | Cheal et al. | |
| 2004/0123806 A1 | 7/2004 | Choi | |
| 2004/0162621 A1 | 8/2004 | Crofford | |
| 2004/0172039 A1 | 9/2004 | Dye | |
| 2004/0193168 A1 | 9/2004 | Long et al. | |
| 2004/0193275 A1 | 9/2004 | Long et al. | |
| 2004/0193276 A1 * | 9/2004 | Maroney et al. | 623/19.14 |
| 2004/0193278 A1 * | 9/2004 | Maroney et al. | 623/19.14 |
| 2004/0210317 A1 | 10/2004 | Maroney et al. | |
| 2004/0225367 A1 | 11/2004 | Glien et al. | |
| 2004/0236341 A1 | 11/2004 | Petersen | |
| 2004/0246895 A1 | 12/2004 | Feyerabend | |
| 2004/0260399 A1 * | 12/2004 | Chieng | 623/22.12 |
| 2005/0004680 A1 | 1/2005 | Saladino et al. | |
| 2005/0010230 A1 | 1/2005 | Crofford | |
| 2005/0010232 A1 | 1/2005 | Crofford | |
| 2005/0033290 A1 | 2/2005 | Nevelos et al. | |
| 2005/0033445 A1 | 2/2005 | Siebel | |
| 2005/0033447 A1 | 2/2005 | Evans | |
| 2005/0043810 A1 | 2/2005 | Mears et al. | |
| 2005/0065532 A1 | 3/2005 | Honl et al. | |
| 2005/0065612 A1 | 3/2005 | Winslow | |
| 2005/0080426 A1 * | 4/2005 | Qian | 606/96 |
| 2005/0113841 A1 * | 5/2005 | Sheldon et al. | 606/88 |
| 2005/0149044 A1 | 7/2005 | Justin et al. | |
| 2005/0154398 A1 | 7/2005 | Miniaci et al. | |
| 2005/0203633 A1 | 9/2005 | Fernandes et al. | |
| 2005/0245934 A1 * | 11/2005 | Tuke et al. | 606/79 |
| 2005/0245936 A1 * | 11/2005 | Tuke et al. | 606/89 |
| 2005/0256585 A1 | 11/2005 | Park et al. | |
| 2005/0256586 A1 | 11/2005 | Kraus et al. | |
| 2005/0258033 A1 | 11/2005 | Kumagai et al. | |
| 2006/0004375 A1 * | 1/2006 | Watkins et al. | 606/94 |

| | | | |
|---|---|---|---|
| 2006/0015111 A1* | 1/2006 | Fenton | 606/80 |
| 2006/0096084 A1 | 5/2006 | Hamilton et al. | |
| 2006/0156069 A1 | 7/2006 | Swoboda | |
| 2007/0162038 A1* | 7/2007 | Tuke | 606/88 |
| 2007/0233136 A1* | 10/2007 | Wozencroft | 606/86 |
| 2007/0299451 A1* | 12/2007 | Tulkis | 606/79 |
| 2008/0215057 A1* | 9/2008 | Willi et al. | 606/88 |
| 2008/0228188 A1* | 9/2008 | Birkbeck et al. | 606/87 |
| 2008/0262626 A1* | 10/2008 | Raugel | 623/22.15 |
| 2009/0163923 A1* | 6/2009 | Flett et al. | 606/89 |
| 2011/0071534 A1* | 3/2011 | Tuke | 606/89 |

FOREIGN PATENT DOCUMENTS

| | | |
|---|---|---|
| DE | 1164019 B | 2/1964 |
| DE | 10056698 A1 | 5/2002 |
| DE | 10335442 A1 | 2/2005 |
| DE | 102004013368 A1 | 10/2005 |
| EP | 0363019 A2 | 4/1990 |
| EP | 457222 | 11/1991 |
| EP | 617934 A1 | 10/1994 |
| EP | 712617 A1 | 5/1996 |
| EP | 715836 A1 | 6/1996 |
| EP | 0768066 A2 | 4/1997 |
| EP | 821924 A1 | 2/1998 |
| EP | 1080702 A2 | 3/2001 |
| EP | 1 290 991 A1 | 3/2003 |
| EP | 1415621 A2 | 5/2004 |
| EP | 1464305 A2 | 10/2004 |
| EP | 1477120 | 11/2004 |
| EP | 1522283 A2 | 4/2005 |
| EP | 1588668 A1 | 10/2005 |
| FR | 2631543 A1 | 11/1989 |
| FR | 2656792 A1 | 7/1991 |
| FR | 2821545 A1 | 9/2002 |
| FR | 2854320 A1 | 11/2004 |
| GB | 1448111 A | 9/1976 |
| GB | 2042897 A | 10/1980 |
| GB | 2333961 A | 8/1999 |
| GB | 2347864 A | 9/2000 |
| GB | 2366733 A | 3/2002 |
| GB | 2372707 A | 9/2002 |
| GB | 2396561 A | 6/2004 |
| GB | 2397765 A | 8/2004 |
| GB | 2406056 A | 3/2005 |
| JP | 2000-312692 | 11/2000 |
| JP | 2002-159516 A | 6/2002 |
| JP | 2004-073854 A | 3/2004 |
| WO | 97/16138 A1 | 5/1997 |
| WO | 97/25943 A1 | 7/1997 |
| WO | 02/17820 A1 | 3/2002 |
| WO | 03/034952 A2 | 5/2003 |
| WO | 03/092556 | 11/2003 |
| WO | 03/093939 A2 | 11/2003 |
| WO | 03/096939 A1 | 11/2003 |
| WO | 2004/107993 A1 | 12/2004 |
| WO | 2004/108020 A1 | 12/2004 |
| WO | 2005051209 A1 | 6/2005 |
| WO | 2005/089676 A1 | 9/2005 |

OTHER PUBLICATIONS

Biomet's ReCap Femoral Resurfacing System, Biomet Orthpedics, Inc., 2004 (1).
Biomet's ReCap Femoral Resurfacing System, Biomet Orthpedics, Inc., 2004 (2).
Birmingham Hip Resurfacing, website printout, www.midmedtec.co.uk, 2 pages, printed Oct. 20, 2005.
Clinical Results of Hybrid Fixed Resurfacing, www.mdmedtec.co.uk, printed Jun. 24, 2004.
Conserve Femoral Surface Replacement, Instrument Listing, Wright Medical Technology, Inc., 2000.
Conserve Plus, Total Hip Resurfacing System, Wright Medical Technology, Inc., 2004.
Cormet Interactive, Corin V BHR, www.corn.co.uk, printed Jun. 29, 2004.
Cormet Interactive, Differences in Acetabular Component, www.corin.co.uk, printed Jun. 29, 2004.
Cormet Operative Technique for the Cormet Metal-on-Metal Hip Resurfacing System, Corin, 2001.
Derek McMinn, Birmingham Hip Resurfacing Operative Technique According to Derek McMinn, University of Birmingham Research Park, 24 pages, 1998.
Development of the BHR, A Comprehensive System, www.midmedtec.co.uk, printed Jun. 24, 2004.
Durom Hip Resurfacing, A Solution for Young and Active Patients, Zimmer, www.centerpulse-orthopedics.com, printed Jun. 24, 2004.
Harlan Amstutz, MD, Conserve femoral surface replacement system, surgical technique, 2005.
Hip Resurfacing Concept, www.midmedtec.co.uk, printed Jun. 24, 2004.
Hip Resurfacing Conserve Plus Femoral Resurfacing Implant, www.wmt.com, printed Jun. 24, 2004.
ICON Metal on Metal Hip Resurfacing, About ICON, www.iconhip.com, printed Jun. 30, 2004.
ICON Metal on Metal Hip Resurfacing, History of Hip Resurfacing, www.iconhip.com, printed Jun. 30, 2004.
Metal/Metal Hybrid Resurfacings, Hybrid Fixed Resurfacing Components, www.midmedtec.co.uk printed Jun. 24, 2004.
Partial European Search Report, EP07111027, Dated May 26, 2010.
Patient Guide to Hip Resurfacing, Clinical Results, www.resurfacingofthehip.com, printed Jun. 24, 2004.
Patient Guide to Hip Resurfacing, Frequently Asked Questions, www.resurfacingofthehip.com, printed Jun. 24, 2004.
Patient Guide to Hip Resurfacing, Resurfacing Hip Replacement, www.resurfacingofthehip.com, printed Jun. 24, 2004.
Patient Guide to Hip Resurfacing, The Implant, www.resurfacingofthehip.com, printed Jun. 24, 2004.
ReCap Total Resurfacing System, Biomet International, 2004.
Stryker Orthopaedics, Hip Systems, Accolade C, Achieving Perfect Balance, www.stryker.com/jointreplacements/sites/primarystems/accoladec.php, printed Jan. 31, 2006.
Stryker Orthopaedics, Hip Systems, Citation TMZF, www.stryker.com/jointreplacements/sites/primarystems/citation.php, printed Jan. 31, 2006.
Stryker Orthopaedics, Hip Systems, Meridian TMZF Beta Titanium Alloy Femoral Component, www.stryker.com/jointreplacements/sites/primarystems/meridian.php, printed Jan. 31, 2006.
Stryker Orthopaedics, Hip Systems, Secur-Fit HA, www.stryker.com/jointreplacements/sites/primarystems/securfitha.php, printed Jan. 31, 2006.
Stryker Orthopaedics, Hip Systems, Trident Ceramic Hip System, www.stryker.com/jointreplacements/sites/trident/healthcare/tech2.php, printed Jan. 31, 2006.
Stryker Orthopaedics, Hip Systems, Trident Ceramic Hip System, www.stryker.com/jointreplacements/sites/trident/healthcare/tech3.php, printed Jan. 31, 2006.
Stryker Orthopaedics, Hip Systems, Trident Ceramic Hip System, www.stryker.com/jointreplacements/sites/trident/healthcare/tech4.php, printed Jan. 31, 2006.
Stryker Orthopaedics, Hip Systems, Trident Ceramic Hip System, www.stryker.com/jointreplacements/sites/trident/healthcare/tech5.php, printed Jan. 31, 2006.
Stryker Orthopaedics, Hip Systems, Trident Ceramic Hip System, www.stryker.com/jointreplacements/sites/trident/healthcare/tech6.php, printed Jan. 31, 2006.
Stryker Orthopaedics, Hip Systems, Trident Ceramic Hip System, www.stryker.com/jointreplacements/sites/trident/healthcare/tech7.php, printed Jan. 31, 2006.
Stryker Orthopaedics, Hip Systems, Trident Ceramic Hip System, www.stryker.com/jointreplacements/sites/trident/healthcare/techmono.php, printed Jan. 31, 2006.
Stryker Orthopaedics, Primary Hip Systems, www.stryker.com/jointreplacements/sites/primarystems/accrefs.php, printed Jan. 31, 2006.
Total Joints, Double Shell Arthroplasty, www.totaljoints.info/doublecup_surface1.jpg, printed Jan. 31, 2006.
Total Joints, Recent Reports on the Results of Surface Replacement Operations, Surface Hip Replacement—a breakthrough at last, www.totaljoints.info/NICE_details.htm, printed Jan. 31, 2006.
Total Joints, Surface Hip Replacement, double cup or double shell, The Principle of the Operation, www.totaljoints.info/surface_hip_replace.htm, printed Jan. 31, 2006.

Total Joints, The Blood Supply of Femoral Head After Surface Hip Replacement, www.totaljoints.info/bloodsupply_surfacehip.htm, printed Jan. 31, 2006.

Wright Medical Technology, Inc., Conserve Plus Total Surface Arthroplasty, Surgical Technique, 2005.

Wright Medical, Conserve Implant, www.wmt.com/conserve/physicians/advantages.asp, printed Jan. 31, 2006.

European Search Report, EP07111027, Dated Sep. 6, 2010.

* cited by examiner

METHOD AND APPARATUS FOR HIP FEMORAL RESURFACING TOOLING

CROSS-REFERENCE TO RELATED APPLICATIONS

This application is a divisional of U.S. application Ser. No. 11/593,168, filed on Nov. 3, 2006, the disclosure of which is incorporated herein by reference.

BACKGROUND OF THE INVENTION

The present invention relates generally to systems, kits and methods for joint prosthesis installation tools. The present invention includes jigs and methods for installing a stemless ball component to a prepared femoral head along an axis defined by the prepared femoral head and jigs for installing a sleeve component for adapting a ball component to a prepared femoral head along an axis defined by the prepared femoral head.

Artificial joint prostheses are widely used today, restoring joint mobility to patients affected by a variety of conditions, including degeneration of the joint and bone structure. Typically, the failed bone structure is replaced with an orthopedic implant that mimics, as closely as possible, the structure of the natural bone and performs its functions. The satisfactory performance of these implants can be affected not only by the design of the component itself, but also by the surgical positioning of the implanted component and the long-term fixation of the implant. Improper placement or positioning of the implant can adversely affect the goal of satisfactorily restoring the clinical bio-mechanics of the joint as well as impairing adequate fixation of the component when implanted.

Orthopedic implants are constructed from materials that are stable in biological environments and withstand physical stress with minimal or controlled deformation. Such materials must possess strength, resistance to corrosion, biocompatibility, and good wear properties. Also, the implants include various interacting parts, which undergo repeated long-term physical stress inside the body.

For these reasons, among others, the bone/implant interface and the connection between various parts of the implant must be durable and resistant to breakdown. This is especially important since installation of an orthopedic implant often involves an extensive and difficult medical procedure, and therefore replacement or revision of the installed implant is typically difficult and traumatic.

The requirements for the useful life of the implant continue to grow with the increase in human life expectancy. Also, as implants improve, younger patients are considered as implant candidates. It is therefore desirable to develop implants that, while durable in their own right, minimize the difficulty of replacement The strength and longevity of implants in large part depend on the bone/implant interface. Various methods of connection are known in the art. For example, a hip joint is a ball-in-socket joint, and includes a rounded femoral head and a cup-like socket (acetabular cup) located in the pelvis. The surfaces of the rounded femoral head and the acetabular cup continually abrade each other as a person walks. The abrasion, along with normal loading, creates stress on the hip joint and adjacent bones. If the femoral head or the acetabular cup is replaced with an implant, this stress must be well tolerated by the implant's bearing surfaces to prevent implant failure.

Depending on the type of bone, the location of the bone within the body and individual characteristics, bone has a wide variation in mechanical characteristics. Bone is generally categorized as trabecular or cancellous bone, which is porous and has an open cancellated structure, and cortical bone, which is dense. Considering the femoral bone of the hip joint, FIG. 1 shows the proximal portion of a femur 1 with the upper portion of the shaft 3, a neck 5 and a head 7. A shaft axis A-A is aligned with the shaft 3 and a head axis B-B is generally aligned with the neck 5. The shaft 3 is primarily composed of cortical bone while the neck 5 and head 7 are primarily composed of trabecular bone with cortical bone at the surface.

Implantable joint prostheses have long been used to provide an artificial hip. When the prosthesis is situated in this position, significant forces such as axial, bending, and rotational forces are imparted to the device. Conventional total hip replacements use an intramedullary stem as part of the femoral prosthesis. The stem passes into the marrow cavity of the femoral shaft. These stem type prostheses are very successful but when they fail the stem can create considerable damage inside the bone. The implant can move about inside the bone causing the intramedullary cavity to be damaged. Because a stiff stem transmits the forces more directly into the femoral shaft, such implants have the further disadvantage that they can weaken the surrounding bone nearer to the hip joint due to stress shielding.

Early designs of femoral prostheses for artificial hips relied primarily on cemented fixation. These cements, such as polymethylmethacrylate, are used to anchor the component within the medullary canal by acting as a grouting agent between the component and the endosteal (inner) surface of the bone. While this method of fixation by cement provides immediate fixation and resistance to the forces encountered, and allows the surgeon to effectively position the device before the cement sets, it is not without problems. Over time, the mechanical properties and the adhesive properties of the bone cement degrade; eventually the forces may overcome the cement and cause the components to become loose due to a failure at the cement/bone or cement/stem interface. Alternative approaches to address the issue of cement failure include both biological ingrowth and press-fit type stems.

Stems designed for biological ingrowth typically rely on the bone itself to grow into a specially prepared surface of the component, resulting in firmly anchoring the implant within the medullary canal. A shortfall of this approach is that, in contrast to components that utilize cement fixation, surfaces designed for biological ingrowth do not provide for immediate fixation because it takes time for the bone to grow into the specially prepared surface. Press-fit stems precisely engineered to fit within a surgically prepared medullary canal may or may not have specially prepared surfaces and typically rely on an interference fit of some portion of the component within the medullary canal of the bone to achieve stable fixation.

The need often arises to replace at least a portion of a hip implant. Prior art designs often require the entire implant to be replaced even if only a portion of the implant fails. Similarly, the entire implant may have to be replaced if the implant is intact but certain conditions surrounding the implant have changed. This is often due to the implant suffering from a decrease in support from the adjacent bone due to stress shielding or other negative effects of the implant on surrounding bone.

Surgeons have sought a more conservative device than an implant using an intramedullary stem as part of the femoral prosthesis. There have been a number of attempts at implants using short stems or femoral caps without stems and requiring less extensive surgery. This type of prosthesis is generally known as a hip resurfacing prosthesis. In the mid-1940's, Judet in France designed a prosthesis whereby the majority of the femoral head was removed and a replacement device was fitted with a peg or nail which passed a short way down the femoral neck. Small movement of the device against the bone caused friction of the bone and the bending loads on the peg often caused them to break out underneath the bony femoral neck. In the mid-1970's, double cup type arthroplasty was tried. There were several designs: Wagner in Germany, an Italian Group, Imperial College London and the Tharies design from Amstutz in California.

These all removed a fair proportion of the femoral bearing surface by turning it down to a cylindrical form or hemispherical form. A metal shell was then fixed with bone cement on the remaining bony peg. The acetabular cup was conventional. Unlike normal total hips, however, which have standard femoral head sizes in the range of 22-32 mm, these double cup arthroplasties have large bearing surface diameters closer to the original hip, typically in a range from 40-60 mm. These latter double cup designs commonly failed either by a crack progressing around the bone cement between the prosthetic femoral shell and the bone or by a fracture of the bone across from one side of the prosthetic femoral component rim to the other.

Current approaches to femoral head resurfacing can be traced back to Amstutz in U.S. Pat. No. 4,123,806. In the '806 patent, a hemispherical cap is cemented to a prepared femoral head while preserving a substantial portion of the femoral head. In U.S. Pat. No. 6,156,069, Amstutz shows a femoral head resurfacing implant having a stem. A similar femoral head resurfacing technique having a stem called Birmingham Hip Resurfacing has been developed by McMinn in the United Kingdom.

These stem-type femoral head resurfacing prostheses consist of a bearing cap provided with a central pin that guides the prosthesis during the insertion. The guiding is important because it ensures that the prosthesis will be seating at the appropriate orientation planned by the surgeon with regard to the bone. A consequence of the misalignment of the prosthesis is a sub-optimal load transfer to the bone that can lead to the failure of the prosthetic joint. Similar to the problems with the prostheses having a stem extending into the femoral shaft, a stem-type resurfacing prostheses requires the surgeon to remove enough bone in the neck of the femur so that it can host the pin of the prosthesis and the stem can contribute to stress shielding. Therefore the stem-type prosthesis is not as bone preserving as a stemless prosthesis, either in the short term or long term.

Notwithstanding the problem of guiding a stemless prosthesis, stemless approaches have been advocated and continue to be developed. A modular approach to a stemless femoral hip resurfacing is shown in U.S. Pat. No. 4,846,841 to Oh. In this approach, a frustro-conical cap is press-fit to a prepared femoral head. A ball component is then attached to and retained by the cap using a Morse taper fit. A similar approach is shown in U.S. Pat. No. 5,258,033 to Lawes and Ling, which shows a ball component cemented either directly to a prepared head or, additionally, retained by a press-fit with a frustro-conical cap. A contemporary approach to stemless femoral head resurfacing is found in co-owned U.S. patent application Ser. No. 11/478,870 entitled, Femoral Head Resurfacing.

All of these more modern hip resurfacing approaches require that the femoral head be prepared to provide a properly oriented and shaped bone interface for the implant by shaping the head. The outer prepared bone interface with the implant is symmetrical around a prepared head axis B-B passing through and established with reference to the central region of the femoral neck and is typically cylindrical or conical but may be a more complex tapering solid of revolution. The proximal portion of the prepared head can be a flat surface, tapered, domed, chamfered, or any combination of these features and is usually performed as a separate resection. If a stem is used, it may be cylindrical, conical or a more complex tapering solid of revolution and is typically short compared to a conventional intramedullary stem. The portion of the bone that hosts the prosthesis must be shaped so that it matches the shape of the prosthesis. The size and shape of the bone may fit exactly the shape and size of the prosthesis or may provide room for cementing to take place or have an excess of bone in a region to allow press-fit fixation, depending on the preferred fixation method.

Because the desired bone shape of the outer implant interface is symmetrical around an axis, a guide wire or pin introduced into the femoral head is typically used to establish the tooling landmark or datum that establishes and defines the prepared head axis B-B. The guide pin provides an axis of revolution for the various measuring and cutting tools used in the preparation process as shown in FIG. 4 and discussed later. When introduced into the femoral head, the guide wire creates a corresponding bore that also provides a datum for the axis B-B in the absence of the guide wire. Based on pre-operative planning, the surgeon initially places the guide wire, either freehand or using measurement and guidance tools based on various anatomical reference points on the femur. In order to place the pin, the pin is driven or inserted in the proximal surface of the femoral head directed toward the greater trochanter and approximately down the mid-lateral axis of the femoral neck. A gauge having an extended stylus that allows measurement of the position of the pin with respect to the neck is then typically used to make a preliminary check of the pin position. By revolving the gauge, the surgeon can evaluate the position of the pin to ensure that the femoral neck will not be undercut when the cutting tool is revolved around the pin. If the surgeon is satisfied that the pin position meets these criteria, the guide wire is used as the axis of revolution for the shaping cutter or reamer to prepare the head to receive the implant.

For a traditional stem-type resurfacing prosthesis, the stem cavity is used to guide the stem and prosthesis into position. Thus, a stem-type resurfacing prosthesis has provided an acceptable method of guiding the prosthesis with respect to the femoral head axis because the stem cavity approximates the head axis datums and the stem serves as tooling to guide the prosthesis along an axis approximating the femoral head axis during installation by engaging the stem cavity.

For a stemless prosthesis, the stem and stem cavity do not exist and the stem cannot serve as tooling to guide the prosthesis. It is desirable to have tooling and a surgical method for use with a stemless prosthesis that allows implanting the prosthesis along the femoral head axis with at least the same accuracy achieved by stem-type resurfacing prosthesis.

SUMMARY OF THE INVENTION

It is an object of the present invention to provide a more successful surface replacement of the femoral portion of a total hip replacement based on a stemless modular approach to femoral hip resurfacing by improvements to the tooling and methods used for implanting the prostheses components.

According to an aspect of the present invention, a jig or tool is used to control the direction of the travel and the seating force vector of a femoral prosthesis component with respect to an axis previously used to create the outer surface of the resected or shaped femoral head surface that will mate with the prosthesis component.

In a first embodiment of the present invention, a tool and method for seating the sleeve component of a two-part prosthesis guides the sleeve on a guide pin or Kirschner wire located in the head axis used as a datum to create the femoral head resection. The sleeve inner and outer distal surfaces are typically in the shape of a truncated cone, but may also incorporate other anti-rotational or locking features. The inner surface of the sleeve is shaped and dimensioned to mate with a prepared femoral head. The sleeve proximal portion has a central hole capable of allowing the guide pin to pass through it. The tool also has a central cannulated bore capable of receiving the guide pin and slidingly journaling on the guide pin to ensure that the tool is aligned with the datum provided by the guide pin. Consequently, the tool and sleeve are aligned with the femoral head axis while seating the sleeve. The tool distal portion has holding features that conform to a portion of the sleeve outer surface and retains the sleeve with suitable features such as detents. Because of the tapered sleeve exterior configuration mating with the holding features, the sleeve will tend to strongly lock with the tool as a result of the force applied to the tool as the sleeve is seated.

In order to remove the tool and overcome this locking force without damaging the bone surface of the prepared femoral head or breaking the sleeve loose from the femoral head, the tool incorporates release features, such as an extractor assembly that forces pins against the sleeve, to release the prosthesis from the tool.

In another aspect of the first embodiment, these releasing features are symmetrical about the tool and femoral head axis in order to insure that the sleeve is not cocked with respect to the axis by the releasing action.

In a further aspect of the first embodiment, a method is provided for using the prosthesis holding tool of the first embodiment. The sleeve prosthesis is first attached to the prosthesis holder. If necessary, bone cement is applied to the interior surface of the sleeve or to the mating prepared femoral head surface. The tip of the guide pin is introduced into the hole of the sleeve and the cannulated bore of the prostheses holder and the holder is used to drive the sleeve along the axis defined by the guide pin until the sleeve is mated with the prepared femoral head. Then sufficient pressure is applied to seat the prosthesis as required by the selected fixation method. The extractor assembly of the prosthesis holding tool is next used to release the sleeve and the prosthesis holding tool can be removed from the guide pin. The guide pin is then removed from the patient, and a ball component is seated on the sleeve using a suitable tool.

In a second embodiment of the invention, a prosthesis holding tool similar to the first embodiment is adapted to be used when the guide pin has been removed prior to using the tool. The prosthesis holder of the second embodiment has a central pin projecting from the distal prosthesis holding portion to pass through the hole in the proximal portion of the sleeve and enter the bore in the prepared femoral head previously occupied by the guide pin. In other respects, the operation and method of the second embodiment is the same as the first embodiment except that, after preparing the femoral head, the guide pin is removed prior to the step of seating the sleeve.

In a third embodiment, the invention is used to seat a ball component rather than a sleeve. In this embodiment, an alignment jig is temporarily attached to the femoral neck. Initially, a pin location guide is fitted on the guide pin projecting from the femoral head which provides a datum. A frame with various translational and rotational adjustments is connected with the location guide, and also fastened to the femoral neck. By adjusting the jig position and locking the various adjusting joints, the guide pin position and consequently the femoral head axis are determined and the alignment jig is constrained to align with the axis. The guide pin is then removed. The partial ball component and a suitable prosthesis holding tool are then engaged with the alignment jig to allow the prosthesis and holding tool to be installed by translating the prosthesis and tool along the head axis B-B to create a secondary datum.

The alignment jig of the third embodiment also has the capability to establish a new axis for the alignment pin if necessary. Upon determining that the previous axis is unsatisfactory, the various translational and rotational adjustments of the jig can be re-adjusted to a new axis location. Then a pin location guide can be reinstalled and used as a guide to drive in a new alignment pin that can, in turn, be used for a secondary re-surfacing of the femoral head. The prosthesis can be installed on the newly prepared head and the prosthesis installed along the new axis as described in the previous paragraph.

In a fourth embodiment, the tooling of the third embodiment is modified to provide a separate axis alignment jig and prostheses alignment jig. The axis alignment jig is fitted directly over the guide pin without the use of a pin location guide to determine the head axis and is used to install a mount, typically a mounting pin, on the side of the femoral neck in a predetermined relationship to the head axis B-B. The axis alignment jig is next removed and then the guide pin is removed. The prosthesis is installed in the prosthesis alignment jig and the jig is aligned with the prepared femoral head axis B-B using the mount on the side of the neck. The prosthesis alignment jig is then used to install the prosthesis in a manner similar to the third embodiment.

It is also an aspect of the invention to provide the various surgical methods described in connection with the embodiments above, along with kits incorporating the various tool and jig components for adapting to differently sized sleeves, ball components, and other variations typically encountered in orthopedic replacements of femoral ball components.

DETAILED DESCRIPTION

Figure 1:
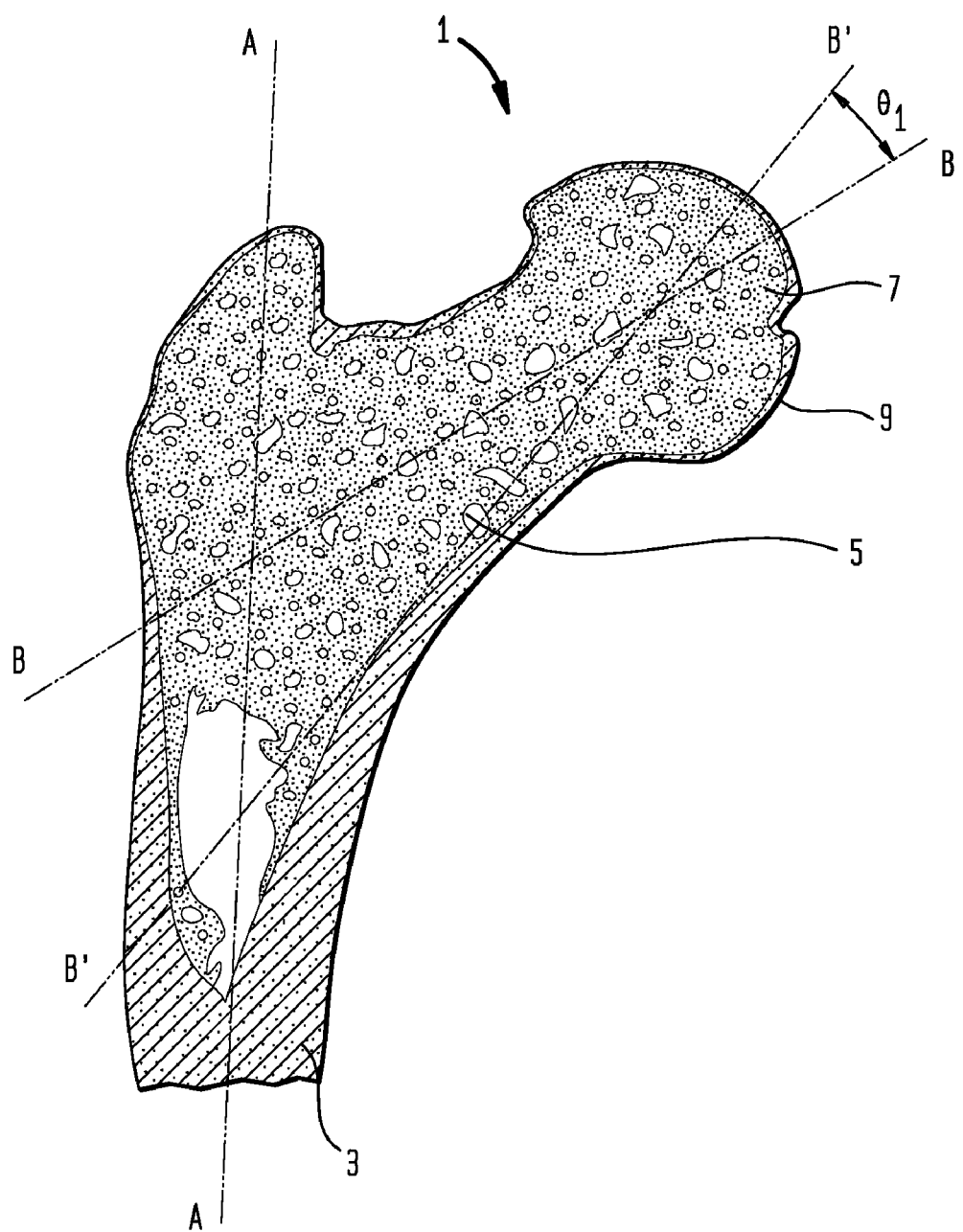
FIG. 1 is a cross-sectional side view of the upper portion of a human femur.
Figure 2:
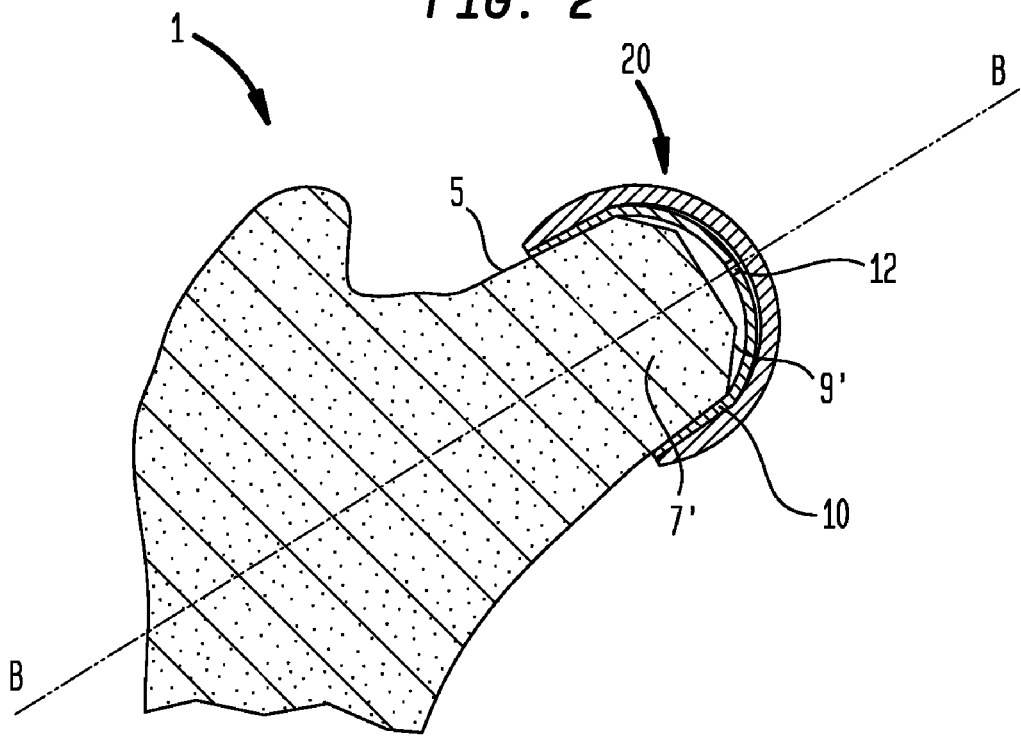
FIG. 2 is a cross-sectional side view of a two-piece femoral resurfacing prosthesis showing a sleeve and ball component installed on a prepared femoral head.

As shown in FIG. 2, a proximal femur as depicted in FIG. 1 has been surgically prepared for the implantation of a stemless femoral hip resurfacing prosthesis. The preparation consists of a re-shaping of the femoral head 7, in this instance, as a surface of revolution about the prepared femoral head axis B-B. The femoral head 7 has been re-shaped by known surgical techniques as a prepared femoral head 7', such that the femoral head surface 9 has been removed, creating a prepared femoral head surface 9'. Arranged in close contact with the distal portion of the prepared femoral head surface 9', is a sleeve 10. In turn, a ball component 20 is fitted over the sleeve 10. The axis B-B passes approximately through the center of the femoral neck 5, the center of the prepared femoral head 7', the center of the sleeve 10, the center of a hole 12 in the sleeve distal end and the center of the ball component 20. In this instance, a two-part modular prosthesis having a sleeve component 10 and ball component 20 is depicted on the prepared femoral head. In some embodiments, a unitary ball prosthesis 20' (not shown), integrating the features of the sleeve 10 and the ball 20 will also be discussed.

Figure 3:
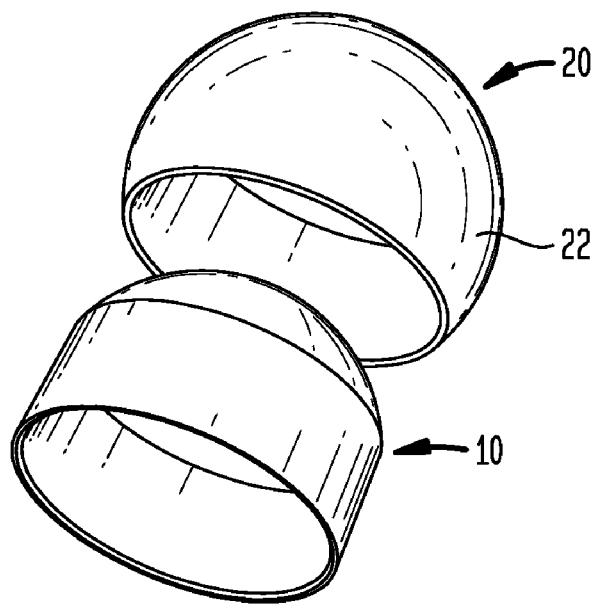
FIG. 3 is a perspective view of a sleeve and ball component corresponding to the sleeve and ball component shown in FIG. 2.

FIG. 3 shows in an exploded perspective view the prosthesis of FIG. 2. It can be seen that the sleeve component 10 fits closely inside at least a portion of the ball component 20. It can further be seen that the sleeve 10 is generally a tapering solid of revolution about a central axis having a sleeve cavity which is configured to interface with the prepared femoral head surface 9'. In this instance, the distal portion of the sleeve is in the configuration of a hollow truncated cone. While shown here in the preferred configuration of a truncated cone, either of the inner or outer surfaces of the sleeve can define any hollow cylinder or tapering surfaces such as an ogive or any parabolic surface capable of being fit over a matched prepared femoral head surface 9'. The proximal portion 12 can be a different shape of revolution about the central axis, for example a flat surface, a spherical domed surface or a chamfered flat surface. When present, the proximal portion 12 may be closely configured to the prepared femoral head surface 9' or may have clearance from the prepared femoral head surface.

The sleeve 10 may be a solid metallic or ceramic structure or it may have a tissue ingrowth surface such as a porous inner surface integrated with or attached to a solid outer layer. The sleeve may also be porous throughout.

The ball component 20 has a spherical outer surface that serves as the bearing for the implant when assembled with a mating acetabular cup. The ball component 20 has a bore that has an inner surface allowing it to closely conform to the distal sleeve outer surface. or in the instance of a one-piece ball prosthesis 20', the prepared femoral head surface 9'. The body of the ball component 20 is preferably made of a metallic or ceramic material similar to those described for the sleeve 10 with the exception that the material is typically solid throughout and has a suitable hardness and durability to provide a bearing surface or substrate. For durability and bearing performance, the ball component 20 may be coated or have a surface layer of ceramic material. In any instance, the hemispherical outer surface must function as a bearing and requires a fine finish. It is also necessary that a prosthesis holder provide suitable handling of the prosthesis to prevent damage to the implant bearing surface during installation.

Figure 4:
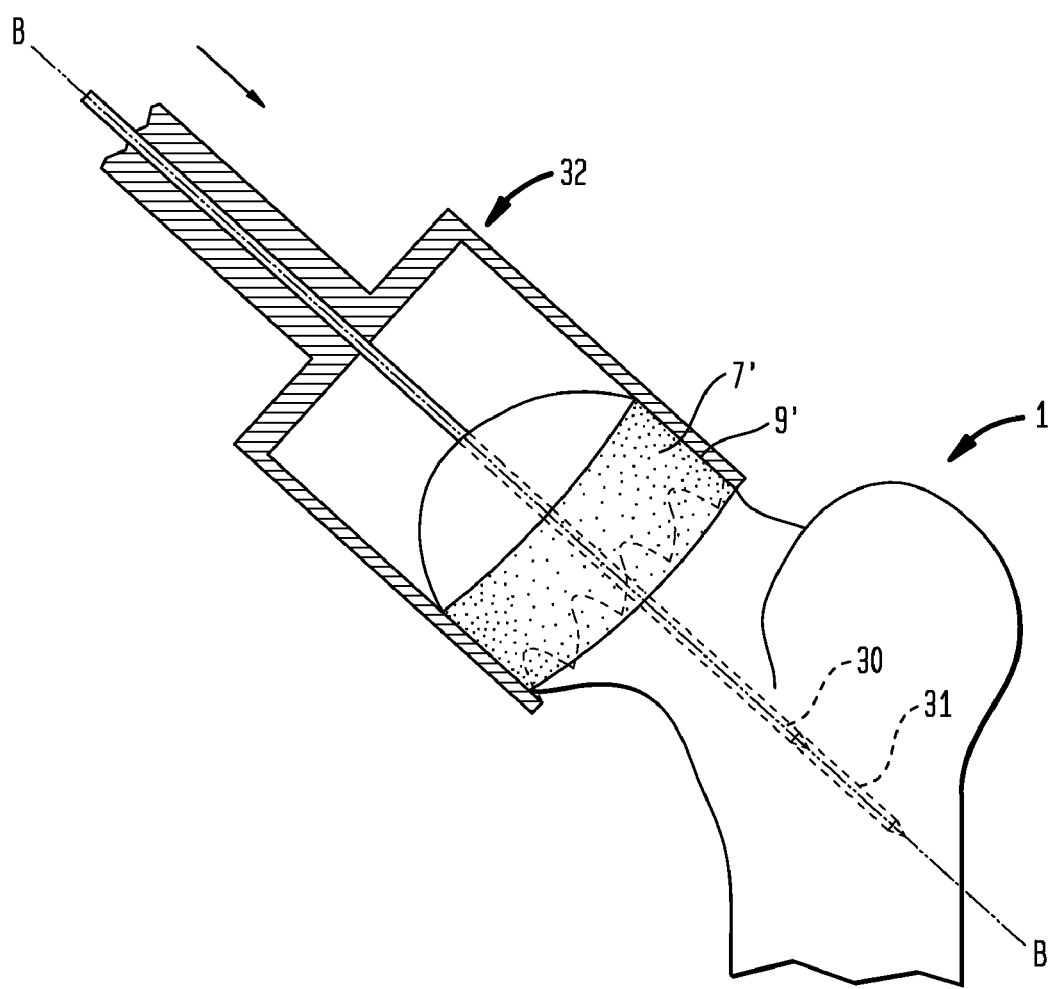
FIG. 4 is a view of a step in the preparation of a femoral head as shown in FIG. 2, wherein a guide pin has been installed along a femoral head axis B-B and is used to prepare a femoral head surface suitable for a prosthesis by revolving a cutter about the pin.

FIG. 4 shows the preparation of the prepared femoral head 7', such that the femoral head surface 9 has been removed to create the distal portion of the prepared femoral surface 9'. The part of the prosthesis that comes in contact with the bone can be tapered, domed, chamfered, cylindered or any combination of any of these features. The portion of the bone that hosts the prosthesis is shaped so that it matches the shape of the prosthesis. The size and shape of the bone may fit exactly the shape and size of the prosthesis or it may provide room for bone cement or provide an excess of bone in some area to allow press-fit fixation, depending on the preferred fixation method. The bone shape is typically symmetrical around a prepared femoral head axis B-B and created by an appropriately shaped cutter 32 that revolves about a guide pin 30, located in a femoral neck bore 31. As shown, the surface 9', the cutter 32, the pin 30 and the bore 31 are co-axial with the axis B-B. The symmetrical axis B-B of the bone is also the axis along which it is desirable to guide the prosthesis for proper installation. The cutter 32 may also shape the proximal portion of the surface 9'.

Figure 5:
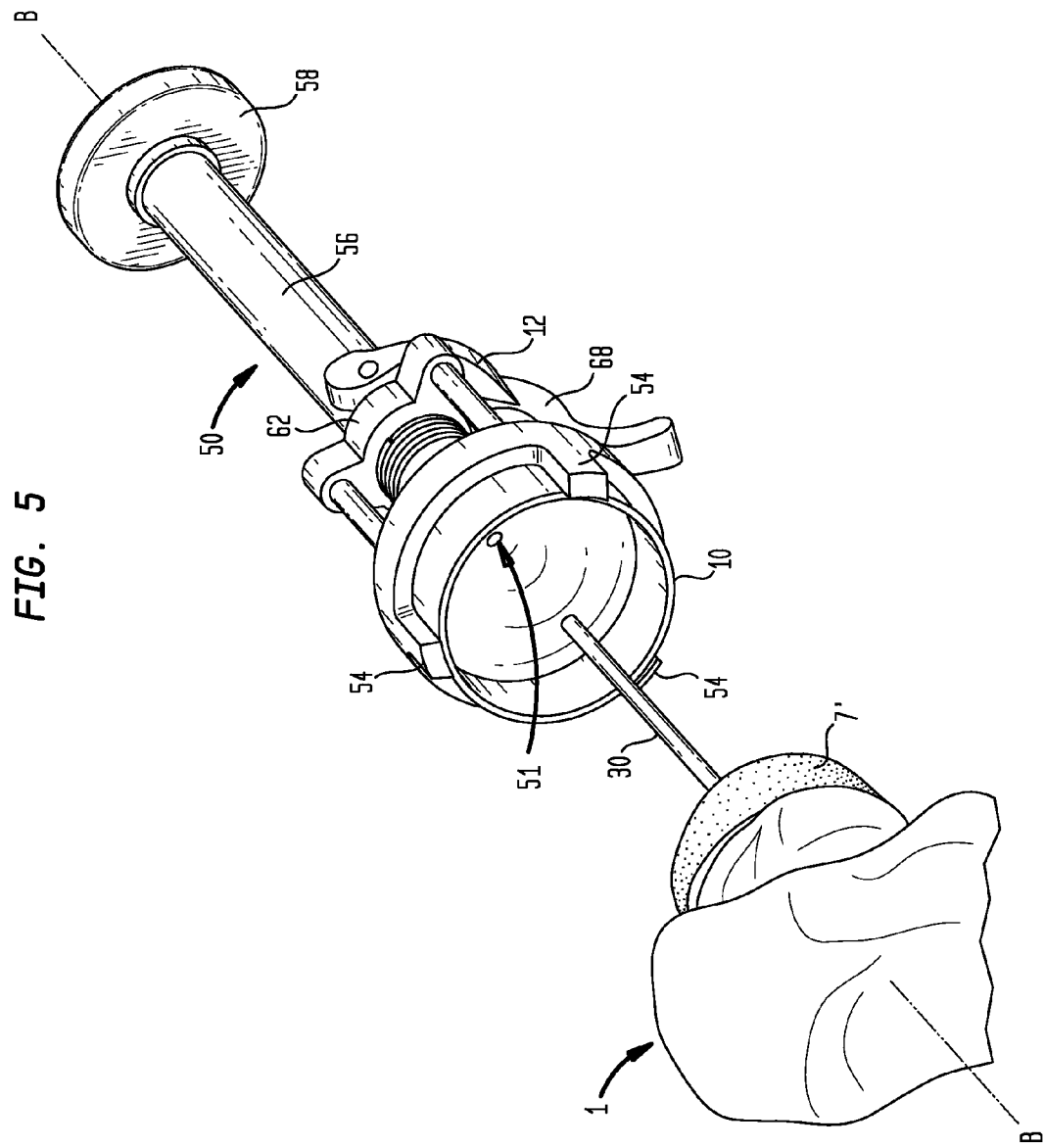
FIG. 5 is a perspective view of a prosthesis holding tool for a sleeve prosthesis according to the first embodiment of the invention.
Figure 6:
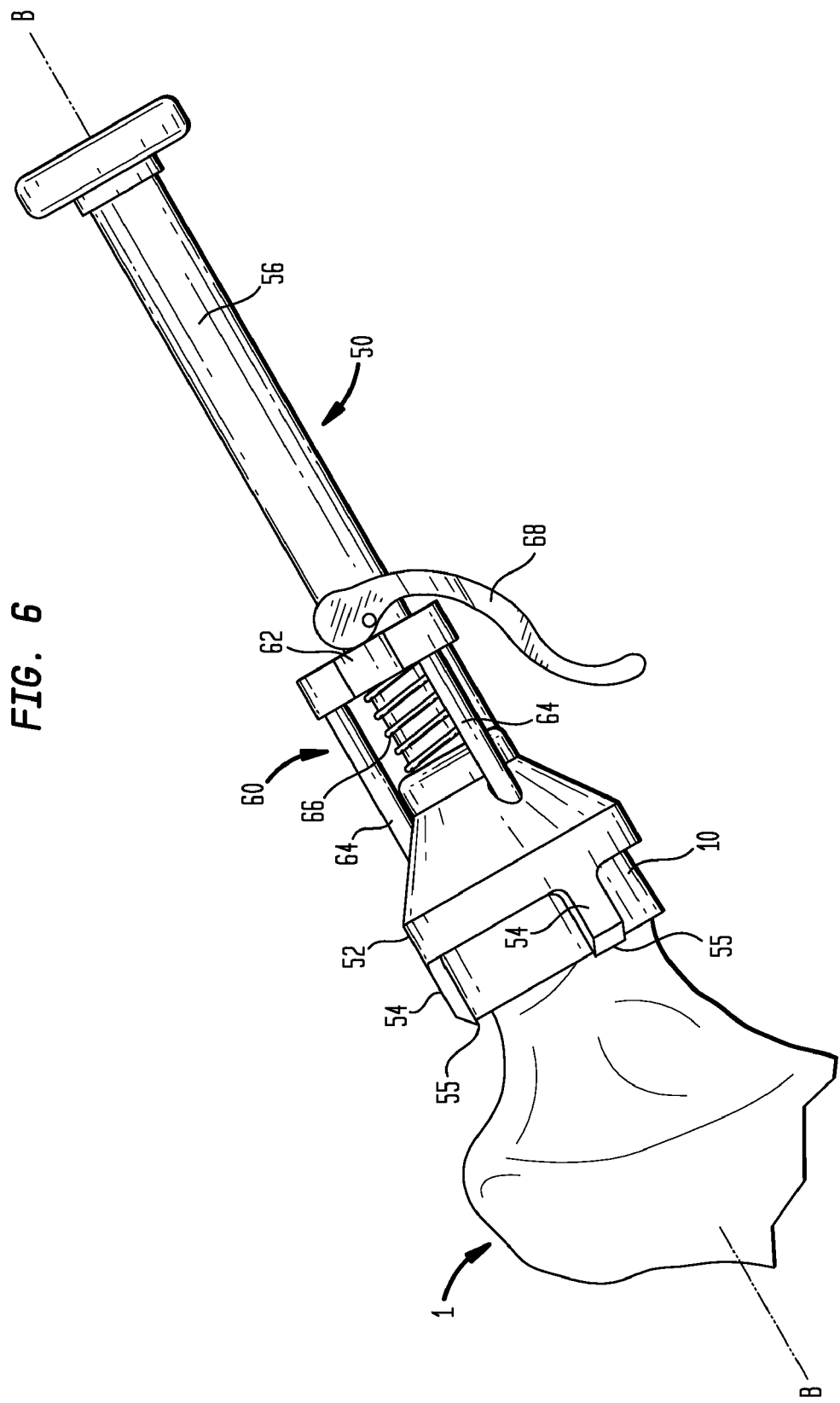
FIGS. 6-10 show perspective views of a sequence of steps in the method of use according to the first embodiment of the invention.

FIGS. 5 and 6 depict a prosthesis holding tool 50 according to an aspect of the first embodiment of the invention for seating the sleeve component 10 of a two-part prosthesis onto the prepared femoral head 7' of the femur 1. The tool 50 is cannulated with a central bore 51 to allow guiding on the guide pin 30 initially used to prepare the femoral head. The sleeve 10 has a central hole 12 in the proximal portion to allow the guide pin 30 to pass through it. The central bore 51 of the tool 50 is capable of receiving the guide pin 30 and slidingly journaling on the guide pin to insure that the tool is aligned with the prepared femoral head axis B-B while seating the sleeve. The tool distal portion has a sleeve interface 52 for receiving the sleeve 10. The sleeve interface 52 has holding features 54 that conform to a portion of the sleeve outer surface and retain the sleeve with suitable features such as detents 55 or tines. Because of the preferred tapered sleeve exterior configuration wedging with the holding features 54, the sleeve 10 will tend to strongly lock with the sleeve interface 52 as a result of the force of seating the sleeve 10 on the head 7'. In order to remove the tool and overcome this locking force without damaging the bone surface of the prepared femoral head 7' or breaking the sleeve 10 loose from the femoral head, the tool incorporates release features, such as an extractor assembly 60 that forces pins 64 against the proximal portion of the sleeve, to release the sleeve from the tool.

It is preferred that the releasing features are symmetrical about the tool and femoral head axis in order to insure that the sleeve is not cocked with respect to the axis by the releasing action. As shown on FIG. 6, the pins 64 are centrally connected and slidingly journalled on the handle 56 of the tool 50 by an extractor cage 62 in order to ensure that the extractor pins 64 apply force symmetrically about the handle axis and consequently the femoral head axis B-B in order to ensure that the sleeve 10 is not cocked during the separation of the tool from the sleeve. A camming lever 68 drives the extractor cage 62 and consequently the extractor pins 64 parallel to the axis B-B when actuated. A return spring 66 is provided to keep the cage 62 positively engaged with the cam of the lever 68.

Figure 7:
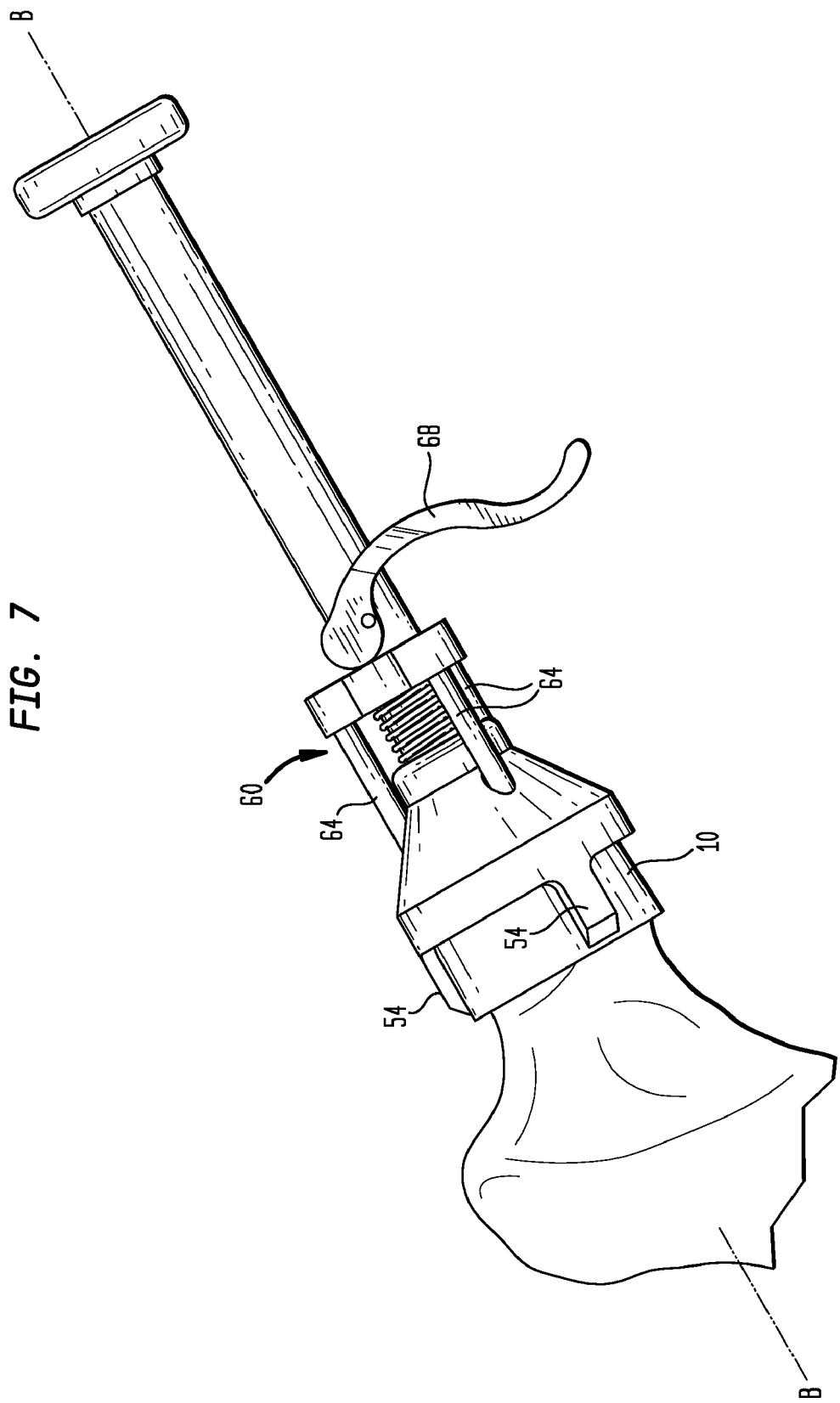
Figure 8:
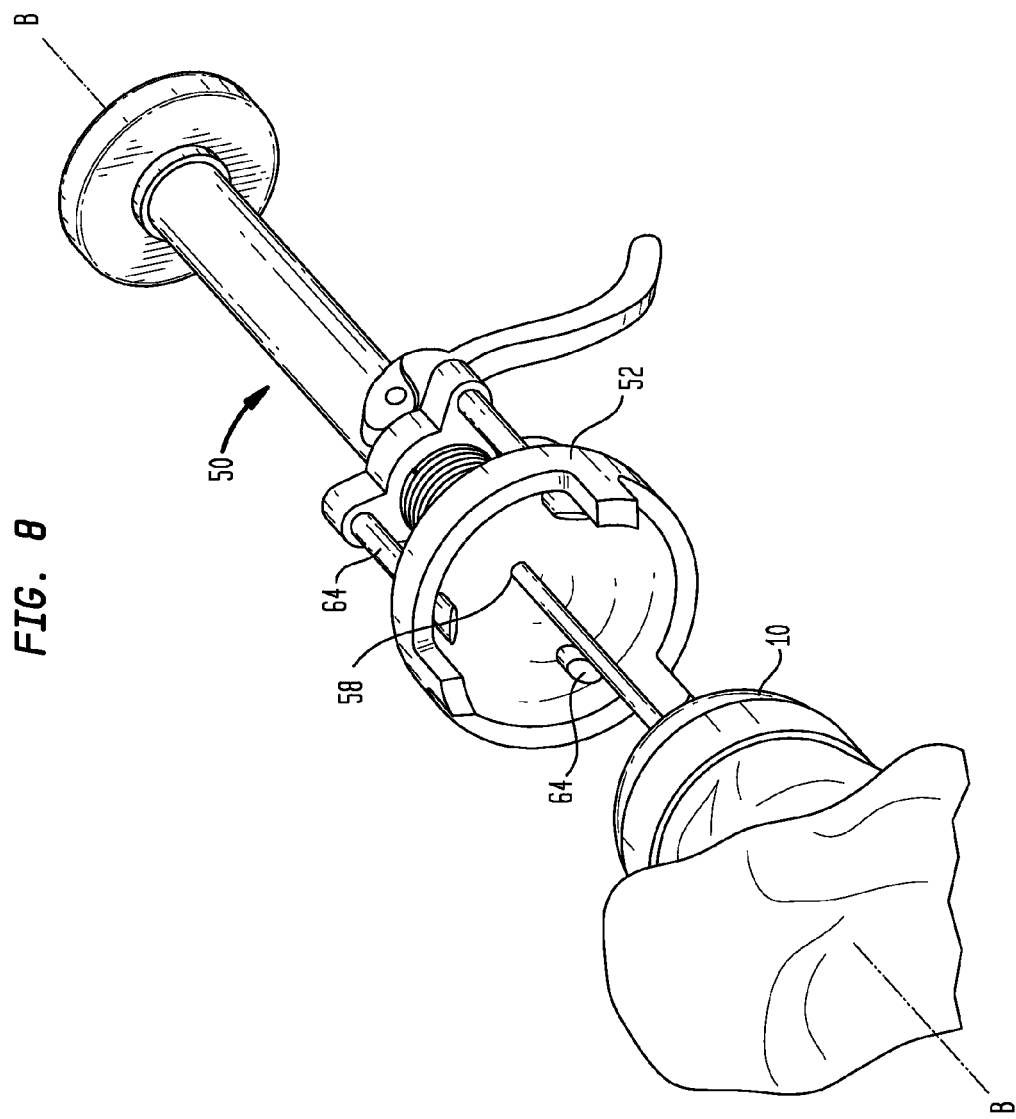
Figure 9:
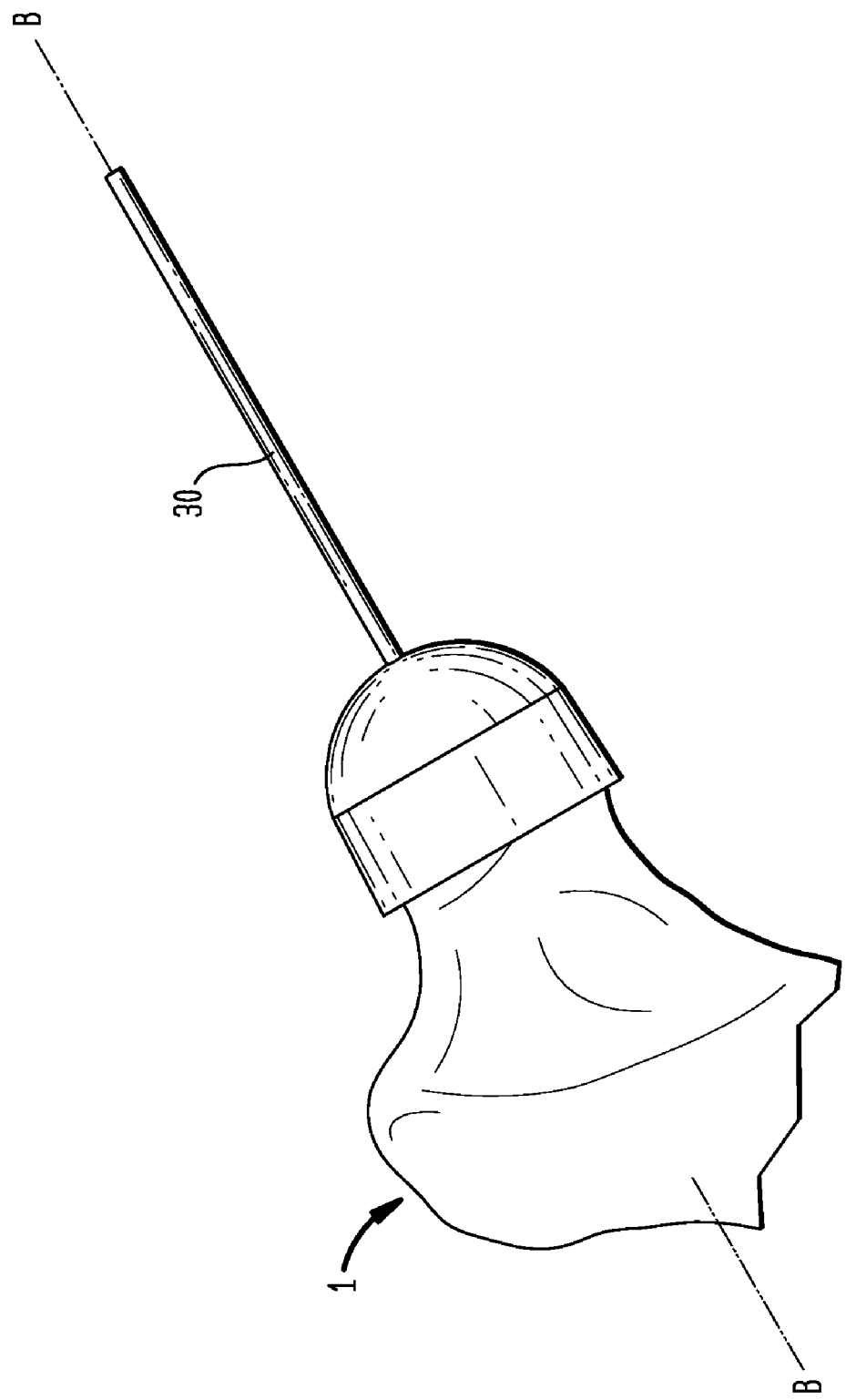
Figure 10:
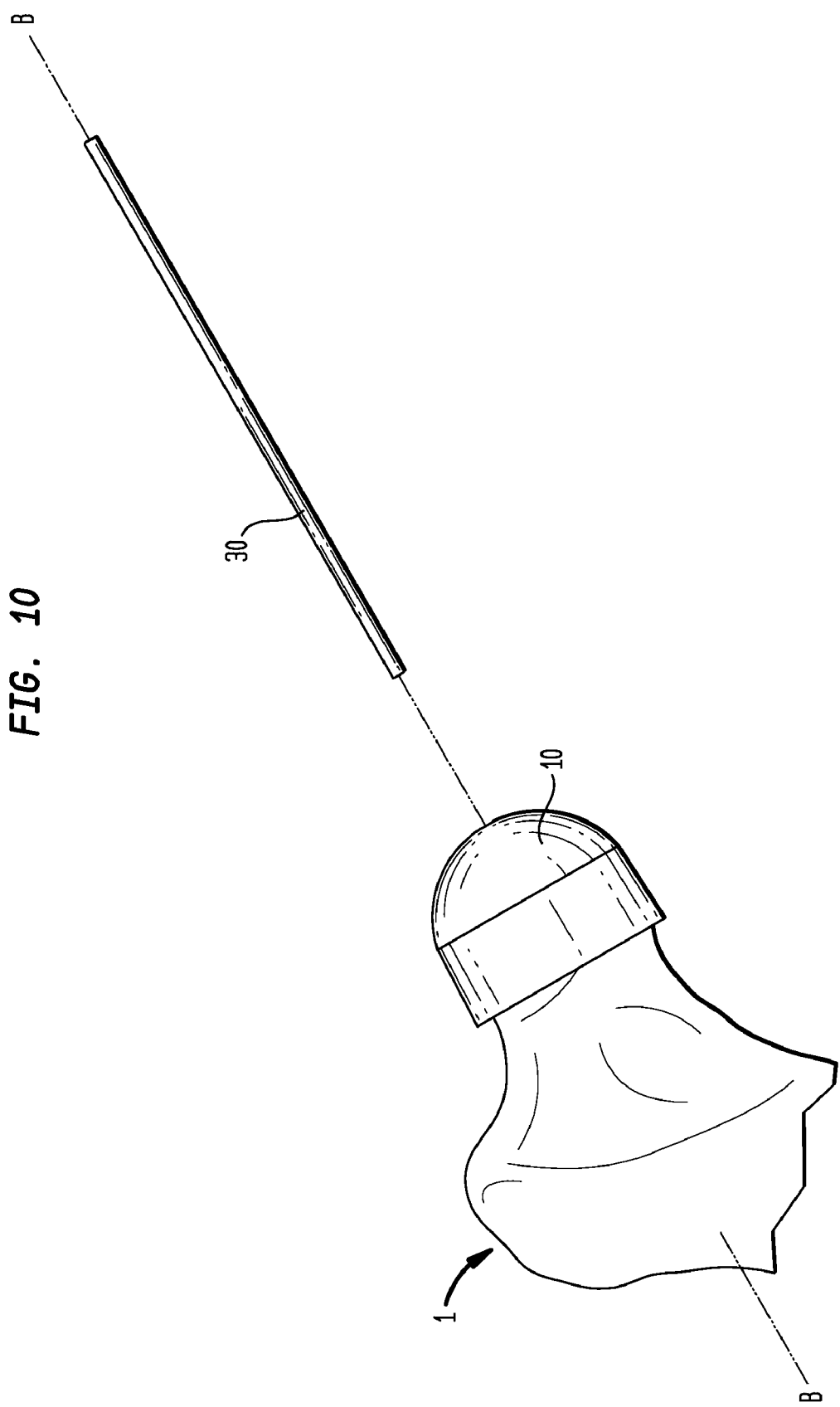

FIGS. 5-10 illustrate the method of using the prosthesis holding tool 50. The sleeve prosthesis 10 is first inserted into the sleeve interface 52 and retained by the tines of the retention prongs 54 located symmetrically about the interface. If necessary, bone cement is applied to the interior surface of the sleeve 10 or to the mating prepared femoral head surface 9'. Using the tool, the sleeve 10 is brought into position to introduce the proximal end of the tip of the guide pin 30 into the central hole 12 of the sleeve and the cannulated bore 51 of the prostheses holder 50. The handle 56 of the holder is used by the surgeon to drive the sleeve 10 along the axis B-B defined by the guide pin until the sleeve is mated with the prepared femoral head 7' as shown in FIGS. 5 and 6. Sufficient pressure is applied to seat the prosthesis as required by the selected fixation method. If necessary, the tool 50 is held in position while the bone cement sets. As seen in FIG. 7, the extractor assembly 60 of the prosthesis holding tool is then actuated by rotating the handle 68 toward the handle 56. As further seen in FIG. 8, this actuation drives the extractor cage and pins 64 distally against the proximal portion of the sleeve 10 to overcome the locking force and detents in order to release the sleeve. The handle 68 is returned to the initial position, withdrawing the pins 64 by the action of the spring 64. The prosthesis holding tool 50 can then be removed from the guide pin 30 as shown in FIG. 9. The guide pin 30 is next removed from the femoral head 7', as in FIG. 10 and a ball component 20 may be seated on the sleeve 10 in a subsequent operation.

Figure 11:
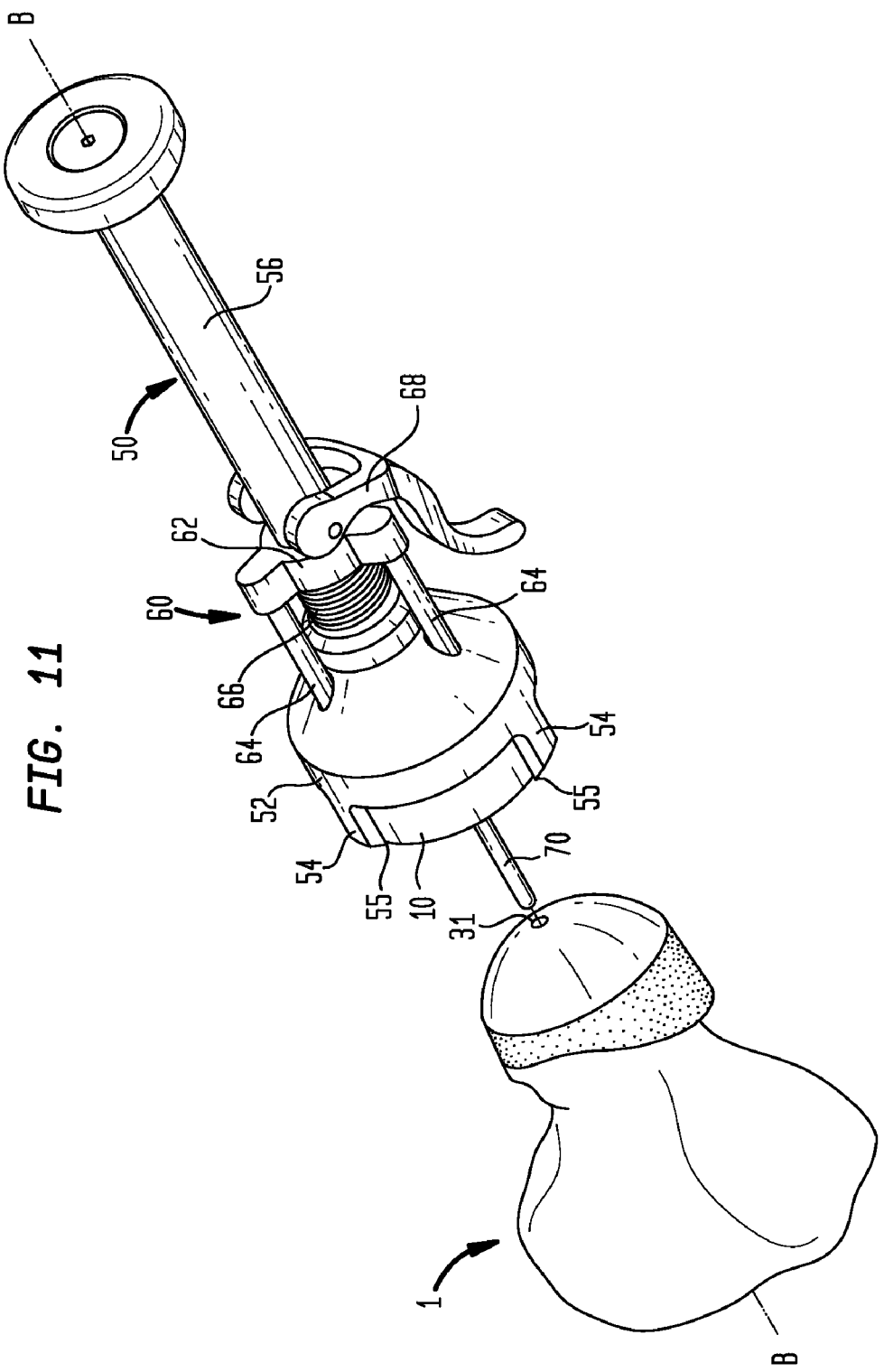
FIGS. 11-12 show the prosthesis holder according to the second embodiment of the invention and the method of use according to the second embodiment of the invention.
Figure 12:
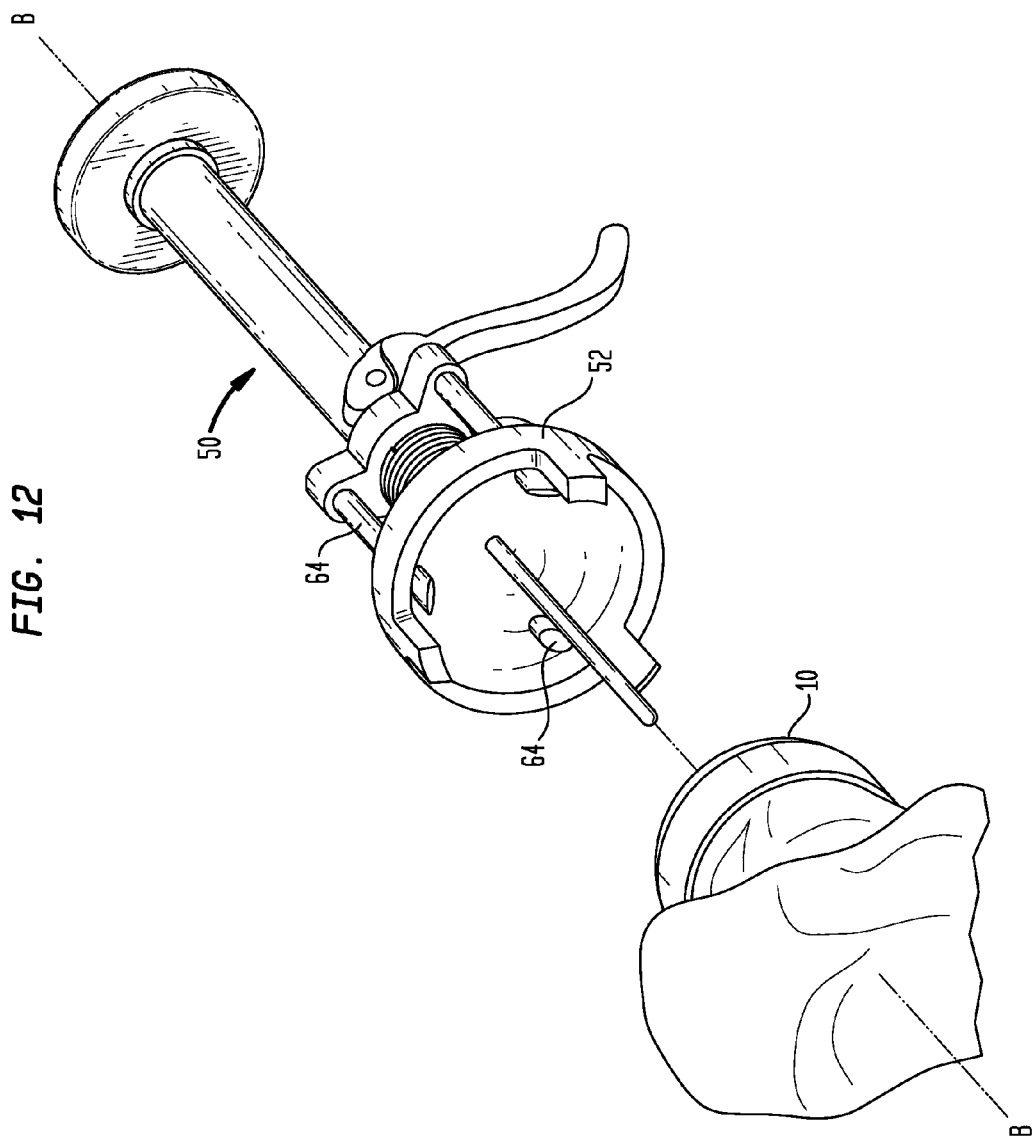

FIGS. 11-12 show a prosthesis holder according to an aspect of the second embodiment of the invention and a sequence of steps of the method of use of the second embodiment of the invention. As depicted in FIG. 11, a prosthesis holding tool 50 similar to the first embodiment is adapted to be used after removing the guide pin 30 prior to being used. After finishing the preparation of the femoral head 7, as previously discussed with respect to FIG. 4, the guide pin 30 is removed from the femoral head 7'.

In order to guide the tool 50, a central alignment pin 70 projects from the center of the handle 56 in place of the bore 51 previously used to receive the guide pin 30. To place the sleeve 10 in the tool 50, the central alignment pin 70 is first passed through the hole 12 in the proximal portion of the sleeve and the sleeve is captured, as in the first embodiment, by the holding features 54 and detents 55 of the sleeve interface 52. As shown in FIG. 11, the tool 50 is positioned with the alignment pin 70 aligned with the axis B-B and guided toward the femoral head 7' until the alignment pin 70 is seated in the bore 31 to slidingly journal the tool along the axis B-B. In other respects, the tool, operation and method of the second embodiment is the same as the first embodiment except that, of course, the guide pin 30 is already removed prior to seating the sleeve.

FIGS. 13-19 show tools and methods according to an aspect of the third embodiment of the invention wherein an alignment jig 80 is attached to a femoral neck 5 to install a ball prosthesis 20' on a prepared femoral head 7' along a prepared femoral head axis B-B determined from the guide pin 30. In this embodiment, the invention is used to seat the ball component 20' rather than the sleeve 10. The ball component 20' depicted is a one-piece type prosthesis with a cavity fitting directly on the prepared femoral head 7' although the aspects of the invention applicable to a one-piece ball component 20' are also applicable to any modular ball component such as ball component 20. Fitting a ball component 20' presents problems because the axis B-B cannot be directly located by the datums of the previous embodiments, either by guiding on the guide pin 30 or the bore 31, during the installation of the ball because the pin must be removed prior to installing the component and the bore is inaccesible as the head 7' enters the cavity 10. As depicted in FIGS. 13-19, an alignment jig 80 is used to transfer the datum for the axis B-B to create a secondary datum at a position sufficiently distant from the femoral head 7' to allow a path for the ball component 20 to be installed on the head. A sequence of steps of the method of using the alignment jig 80 is illustrated in FIGS. 13-19 including, starting in FIG. 16, the use of a prosthesis holding tool 50 guided by the jig to install the prosthesis.

Figure 13:
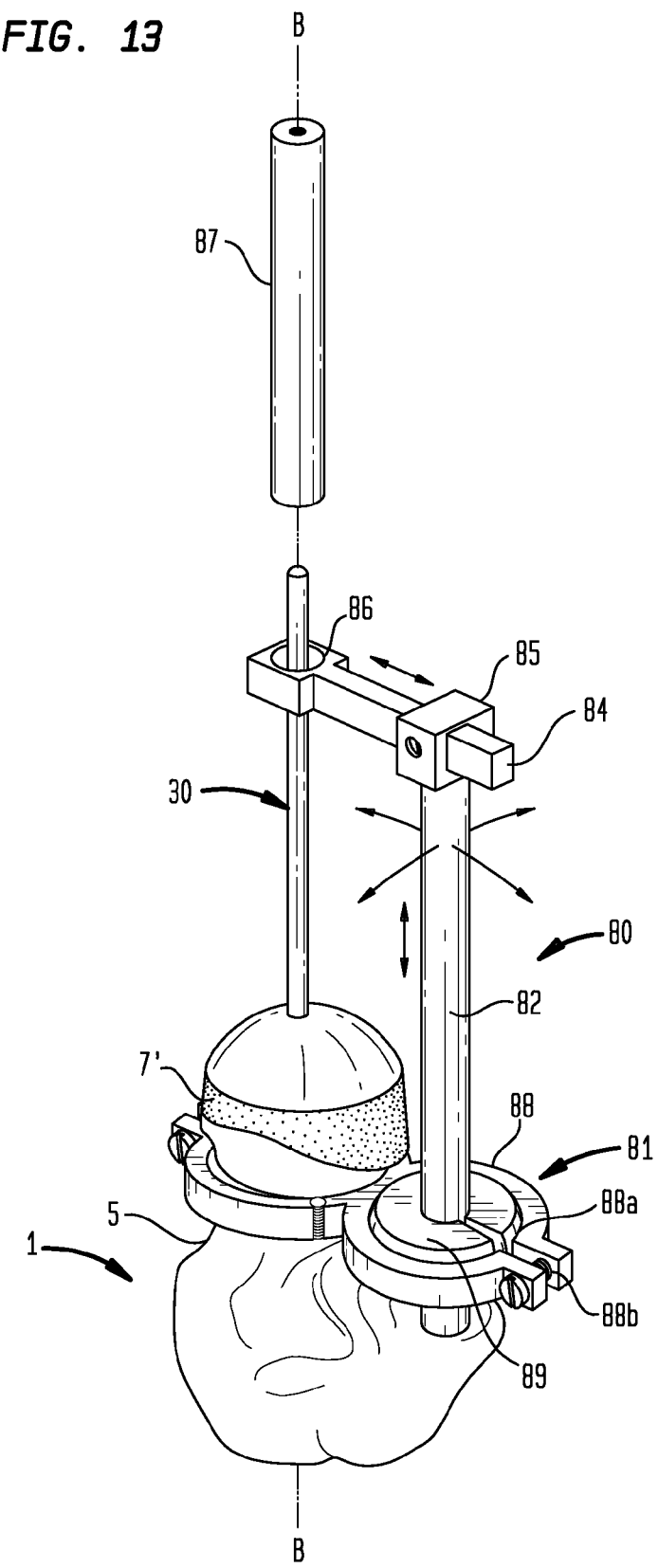
FIG. 13 is a perspective view according to the third embodiment of the invention showing an alignment jig attached to a femoral neck to install a ball prosthesis on a prepared femoral head along femoral neck access.

Turning to FIG. 13, the alignment jig 80 is attached to a proximal portion of the femur 1, preferably at the femoral neck 5. The femoral head 7 has been prepared, as previously discussed with respect to FIG. 4 and the guide pin 30 is temporarily left in place. The alignment jig 80 is comprised of a femoral mount 81, an axial extension 82 and a radial extension 84 with a pin location guide 86 at the proximal end of the extension. The pin location guide 86 is an aperture having a central axis that can be aligned to be co-axial with the femoral head axis datum provided by the guide pin 30 or the bore 31 and consequently with axis B-B. The jig 80 has various clamps, slides and rotational adjustments that provide sufficient degrees of freedom to allow the pin location guide 86 to be co-axially positioned with axis B-B. The pin locator 87 has a bore with a central axis. The bore is sized to slidingly engage on the guide pin 30 projecting from the femoral head and the locator 87 has an outer surface coaxial with the bore that slidingly engages the pin location guide 86 to translate the datum for the axis B-B originally established by the guide pin 30. Alternatively, the pin locator 87 may also be configured with a projecting alignment pin, to locate the datum for axis B-B using the bore 31 in the same manner as the pin 70 of the tool 50 in the second embodiment of the invention.

The femoral mount 81 is first attached to the proximal femur 1, preferably at the femoral neck 5. The attachment may be by friction means using, for example, a hinged clamping mechanism, as shown, or by set screws or bone screws, care being taken to not compromise the integrity of the femoral bone at the interface with the clamp. The mount 81 incorporates a multi-axis adjuster 88 comprising a spherical cavity 88a and a binder bolt 88b. The spherical cavity 88a engages a split spherical collet 89 and can apply a clamping force using the binder bolt 88b as shown. The collet 89, in turn, is slidingly engaged with the axial extension 82 which passes through a central cavity of the collet to provide an axial adjustment. Consequently, when the adjuster 88 is not clamped, the spherical interface 88a provides the collet 89 with three degrees of rotational freedom and allows the axial extension 82 to translate relative to the collet. When clamped, the three rotational degrees of freedom and the translational degree of freedom are locked because the binder bolt 88b constricts the spherical cavity 88a onto the split collet 89, which in turn constricts the collet onto the axial extension 82. Two of the rotational degrees of freedom allow the axial extension 82 to be positioned parallel to the guide pin 30 and axis B-B while the third degree of freedom allows rotation of the axial extension 82 about its axis.

The axial extension 82 has a radial adjustment 85 at its proximal end with a suitable clamping mechanism, such as a set screw, to slidingly engage the distal portion of the radial extension 84 and lock the joint when desired.

Figure 14:
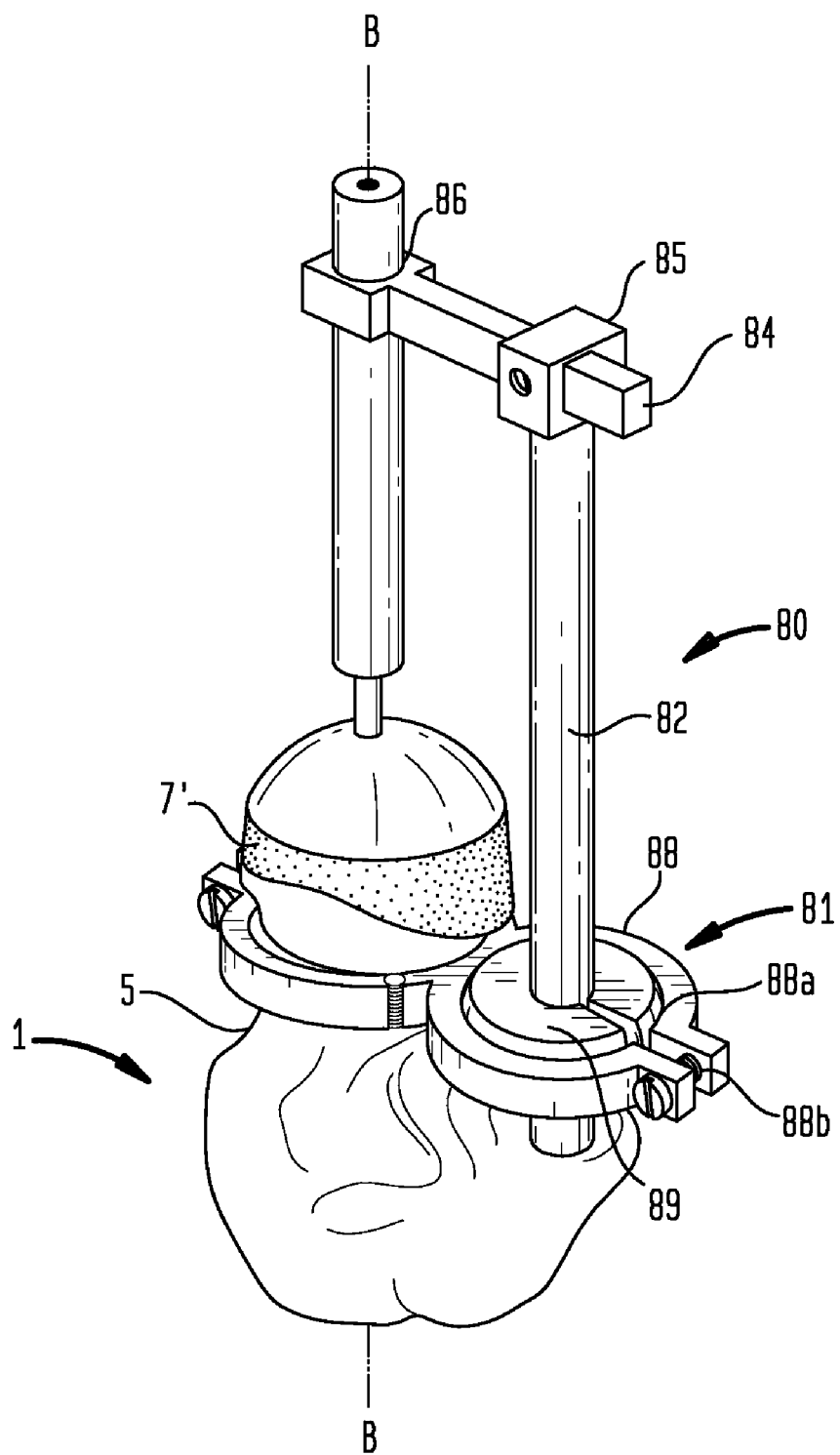
FIGS. 14-19 show perspective views of a sequence of steps of a method of using the alignment jig of FIG. 13 including, starting in FIG. 16, the use of a prosthesis holder guided by the jig to install the prosthesis.

As shown in FIG. 14, when the jig 80 is mounted on the femoral neck 5 and the jig joints are adjusted and locked to allow the pin locator 87 to engage the pin location guide 86, the datum provide by the guide pin 10, and consequently the prepared femoral head axis B-B, are determined and the pin alignment guide 86 is constrained to align with the axis and bore of the guide. The pin alignment guide 86 can now be used as a new datum to determine the axis B-B.

It will be understood by the person of skill in the art familiar with mechanism design and kinematics that numerous configurations of joints, extensions and locking mechanisms will provide the necessary ability to reestablish the datum of axis B-B at a point remote from the surface of the femoral head so long as the necessary degrees of freedom are provided and that the configuration shown is but exemplary. Examples of similar joints, extensions and locking mechanisms indicative of the skill in the art can be found, for example, in a prosthetic checking jig disclosed in U.S. Pat. No. 6,203,575. It will also be recognized by the person of skill that it may be desirable to provide additional redundant rotational and translational axes and appropriate bearing configurations to improve assembly sequences, flexibility of the jig and ease of use, for instance by allowing sideways access to the pin location guide 86. The number of necessary degrees of freedom in the jig 80 may also be reduced by allowing the mount 81 to be adjusted to various positions relative to the femoral neck 5 in order to provide additional degrees of freedom at the neck interface. Supplementary tools, such as a checking fixture to determine that the axial extension 82 is parallel to the guide pin 30 by locating on the guide pin and the extension, may be used to simplify establishing the new datum. While the use of the pin locator 87 is a preferred embodiment, an extended pin 30 may be directly engaged by the pin location guide 86 to determine the datum.

Figure 15:
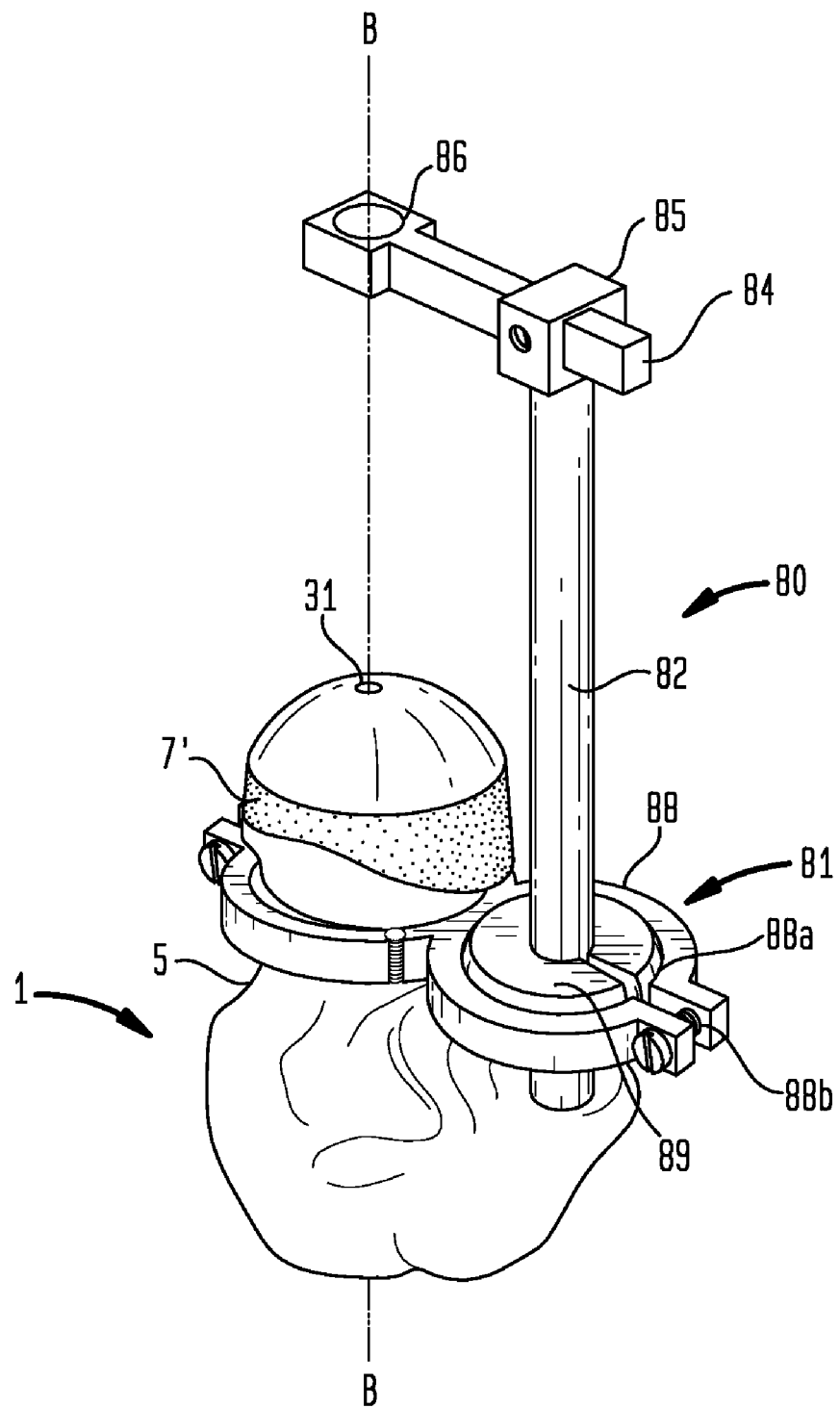
Figure 16:
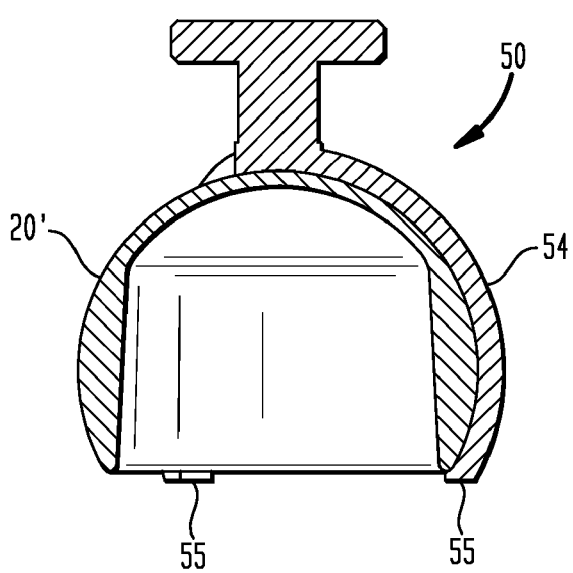

Having established a new datum for the axis B-B, the guide pin 30 is then removed as shown in FIG. 15. In FIG. 16, the partial ball component 20' and a prosthesis holding tool 50 adapted to retain a ball component are mounted on the alignment jig 80 to allow the ball 20' to be installed by translating the prosthesis and tool along the axis B-B as established by the jig using the new datum remote from the femoral head.

Figure 16A:
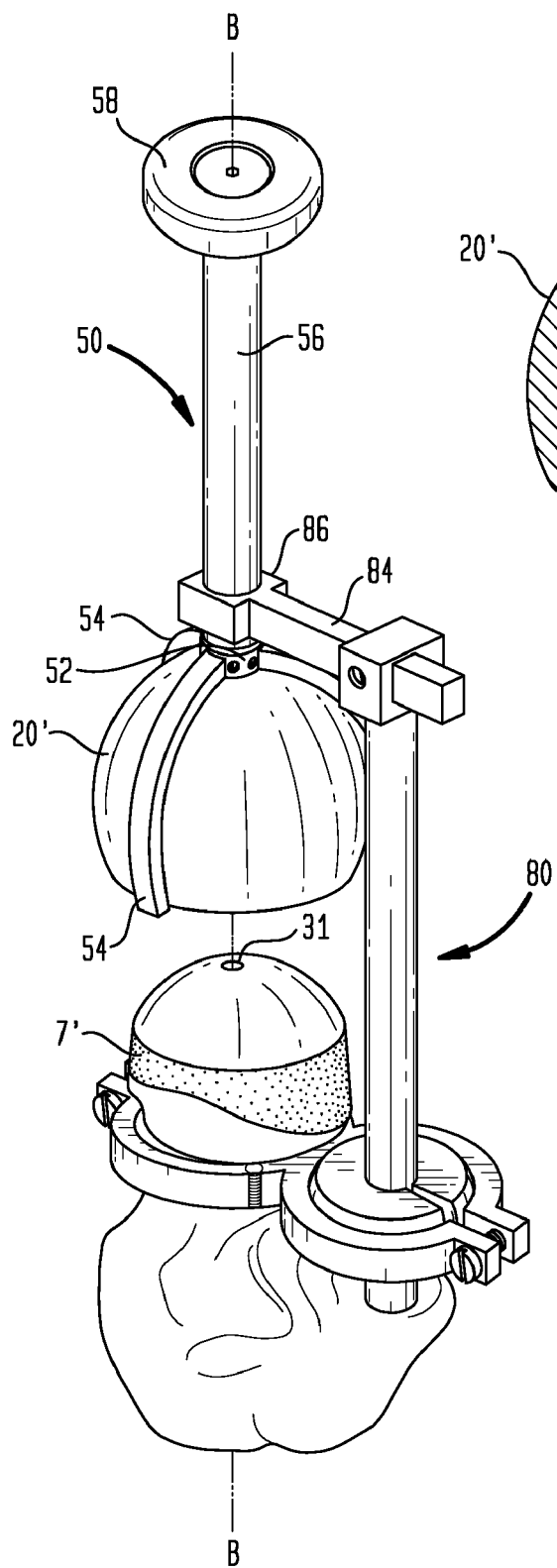

The prosthesis holding tool 50 has been modified to retain and selectably release the ball component 20'. As previously discussed the ball component 20' has a finely finished bearing surface that must be suitably handled to protect the finish. In this example, the ball 20' is gripped by three retention prongs 54, that are pivotably mounted to an interface body 52. The prongs 54 may be capable of elastic deformation or spring loaded and may be released by a suitable pivot arm connected to a release button in the handle 58 as will be understood by a person of skill in the art. If desired, detents 55 or tines, may be engaged on the planar portion of the partial ball component 20' to prevent rotation of the ball as shown in FIG. 16A. The tines 55 project inwardly from the spherical inner surface of the prongs 54 at the position corresponding to the planar portion of the partial ball component 20'. In use, the prongs 54 are deflected outward to install the ball component 20' and capture the ball component when the ball component is fully seated and the prongs 44 and tines 55 move inward. The ball 20' may be released by overcoming a spring preload or deflecting the retention prongs 54 and tines 55 either as a result of the frictional retention force created by the interface of the ball cavity with the prepared femoral head surface 9' as the tool 50 is retracted or by a plunger acting on the ball to eject it from the tool. Methods of protecting, retaining and releasing a ball component 20 or 20' are known as disclosed in U.S. Pat. No. 4,542,825; U.S. Pat. No. 5,133,765; U.S. Pat. No. 6,585,771; and U.S. Published Patent Application No. 2003/0228357.

Figure 17:
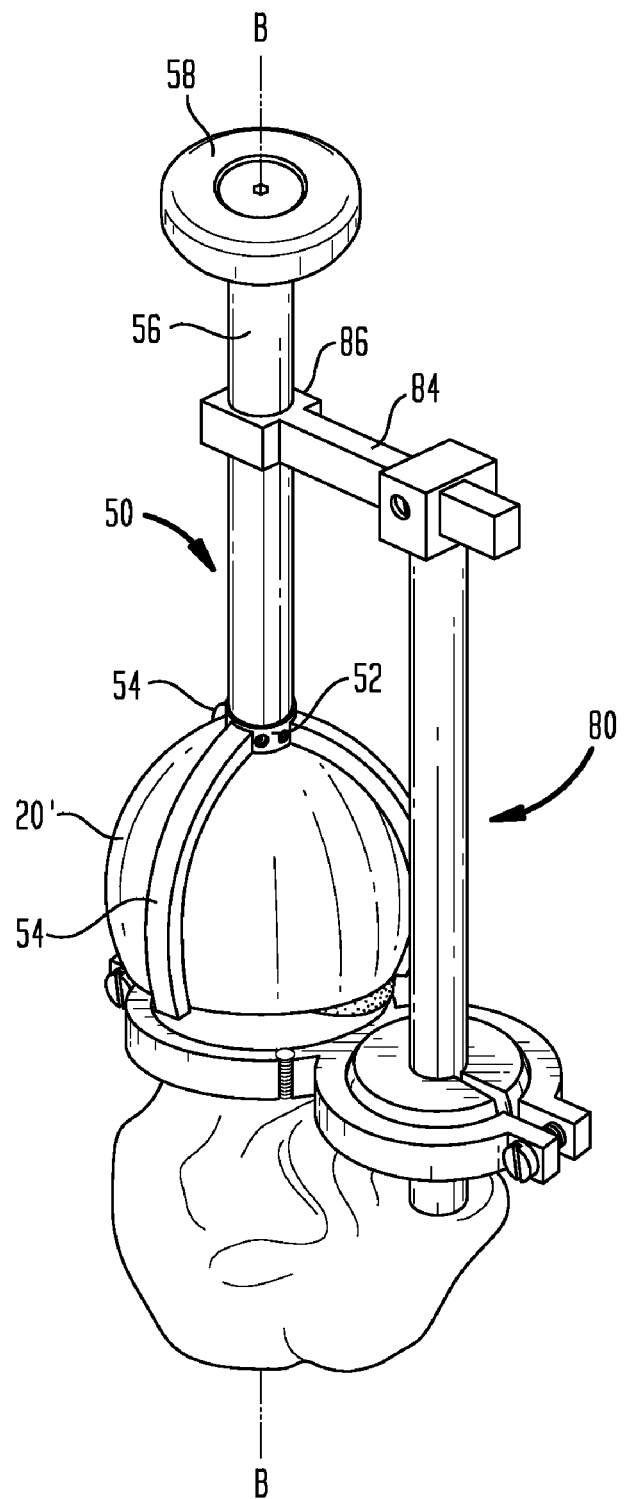
Figure 18:
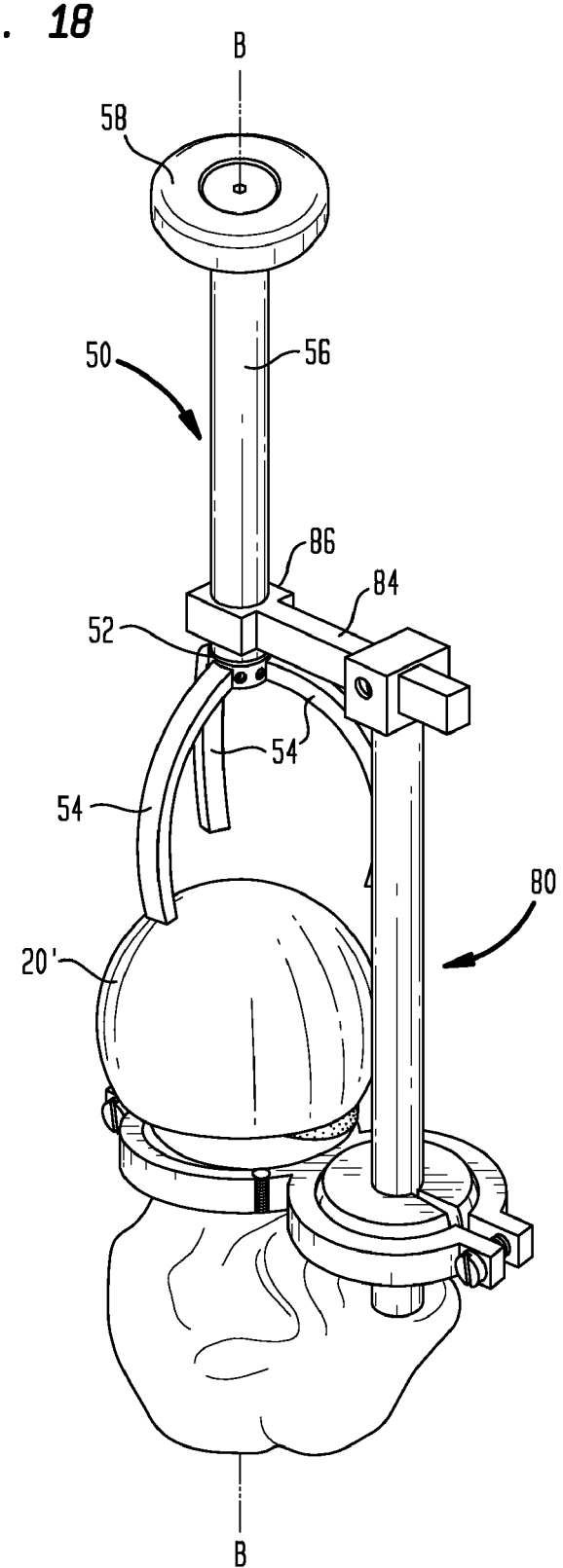
Figure 19:
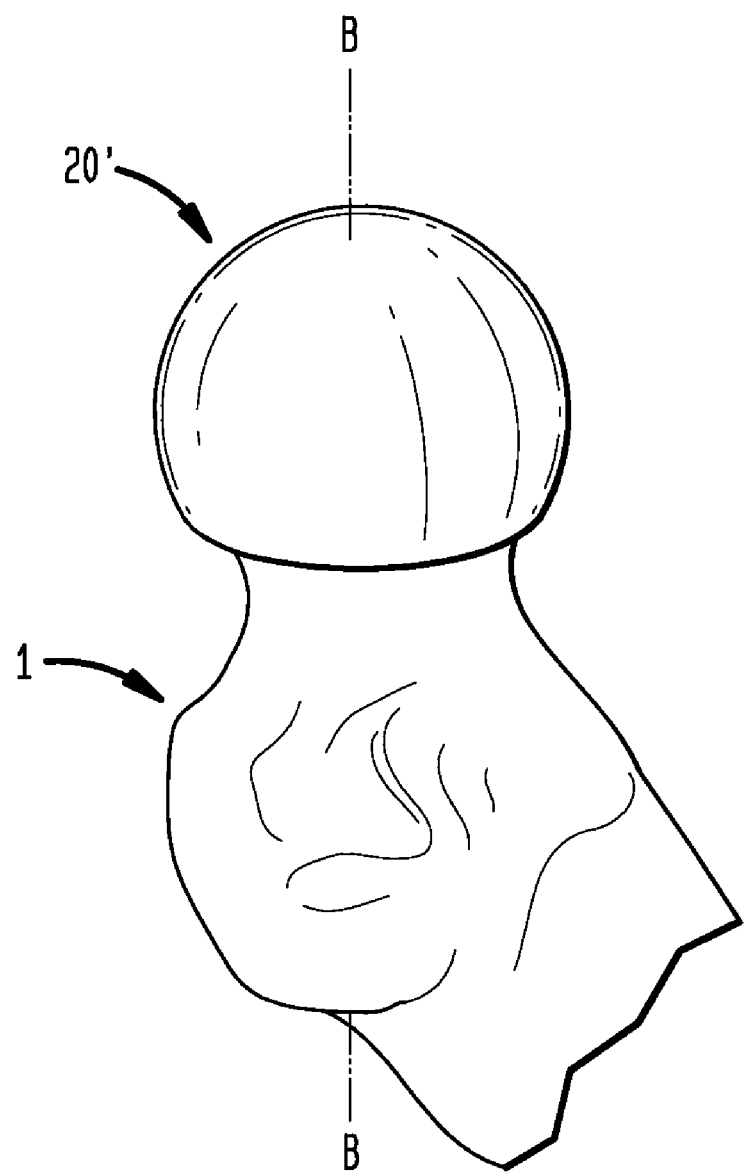

The prosthesis holding tool 50 is guided along the axis B-B by the sliding engagement of the cylindrical tool handle 56 with the bore of the pin alignment guide 86 that is now used as a new datum to determine the axis B-B and control the path of the tool and consequently the ball component along the axis until seated on the prepared femoral head 7' as shown in FIGS. 17 and 18. In FIG. 18, the ball 20' has been released from the retention prongs 54 and the tool retracted and subsequently removed as shown in FIG. 19.

FIGS. 20-26 show a sequence of perspective views according to a fourth embodiment of the present invention similar to the third embodiment except that the datum for the axis B-B is not absolutely determined and the tooling is simplified by the use of a separate axis alignment jig and prostheses alignment jig. First, the axis alignment jig 90 is used to determine the position of a secondary alignment pin on the side of the femoral neck relative to the axis B-B, then the axis alignment jig is removed and the prosthesis alignment 100 is engaged on the secondary pin to install the ball component prosthesis.

Figure 20:
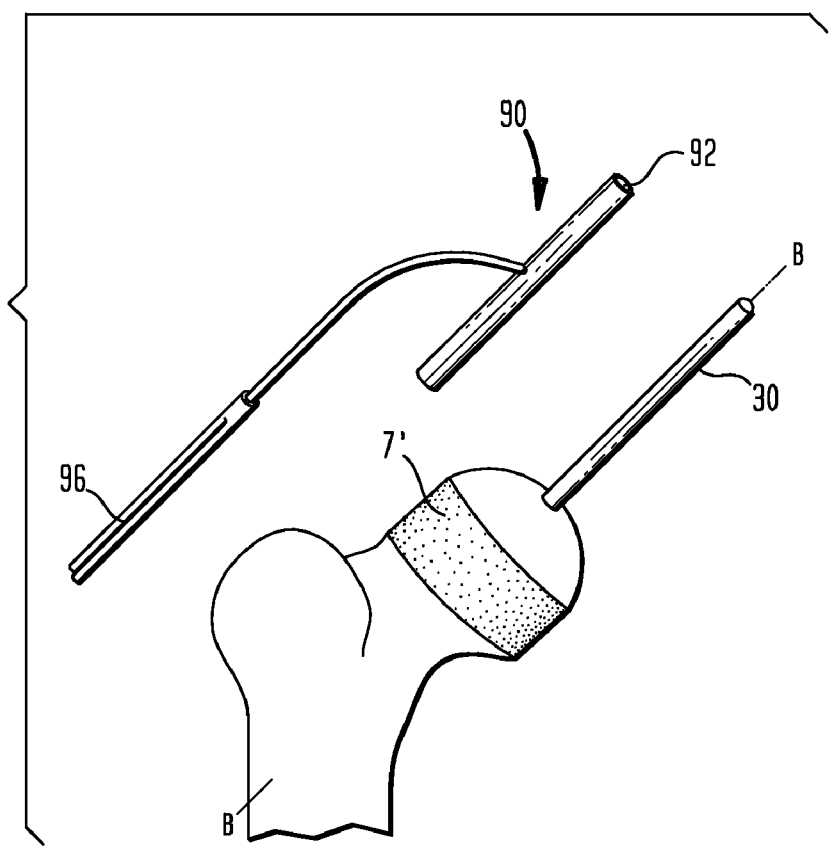
FIGS. 20-26 show a sequence of perspective views according to a fourth embodiment of the present invention and the method of use of an alignment jig to determine the position of a secondary alignment pin on the side of the femoral neck using an alignment jig and then using a separate prosthesis holder engaged on the secondary pin to install the ball component prosthesis.
Figure 21:
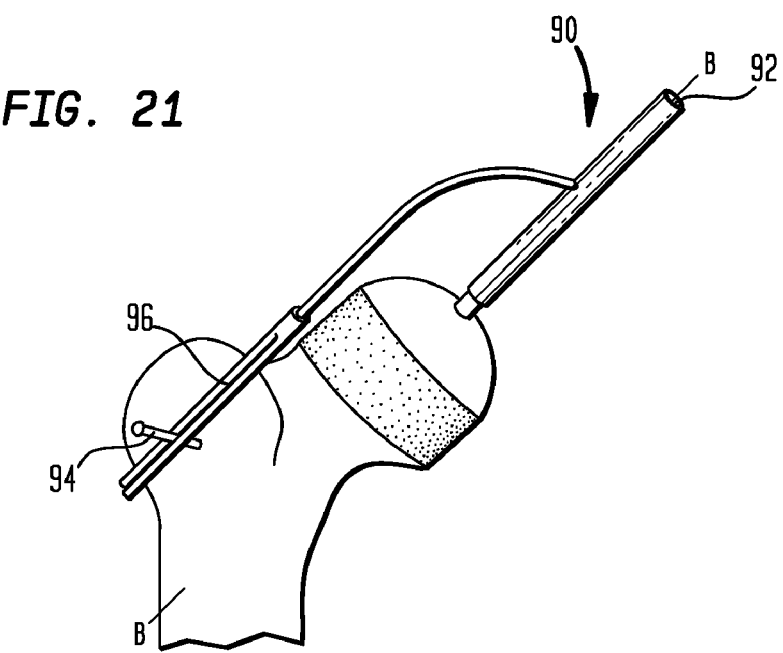
Figure 22:
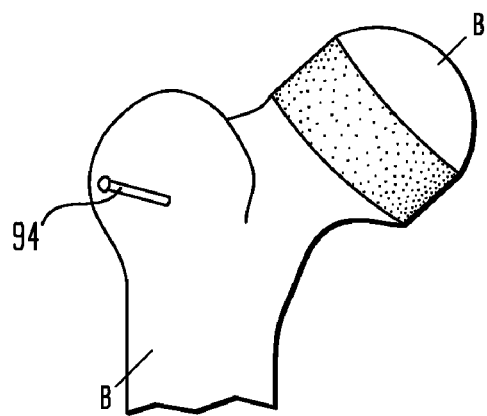

As shown in FIG. 20, the axis alignment jig 90 has, at its proximal end, a tube with a bore 92 sized to slidingly engage and journal the guide pin 30. As in the other embodiments, the guide pin 30 is the datum for the axis B-B of a prepared femoral head 7'. The jig 90 has an extension having a slotted fitting 96. The jig is placed with the bore 92 directly over the guide pin to locate the datum for axis B-B. A mount, typically a mounting pin 94, is then placed on the side of the femoral neck in a predetermined relationship to the axis B-B determined by the slot in the fitting 96 as shown in FIG. 21. It can be seen that an axis defined by the pin 94 will intersect the axis B-B because the slot orients the pin 94 to intersect the axis B-B. Typically, the surgeon places the pin approximately perpendicular to the axis B-B in a freehand manner, but a supplemental tool establishing an axis perpendicular to the axis of the bore 92 for guiding the pin 94 may be mounted proximal to the slot of fitting 96 to insure that the pin 94 is perpendicular to the axis B-B by using, for instance, a bore in the supplemental tool that is perpendicular to the axis when mounted to the fitting 96 to guide the pin. As shown on FIG. 22, the axis alignment jig 90 is then removed followed by the guide pin 30.

Figure 23:
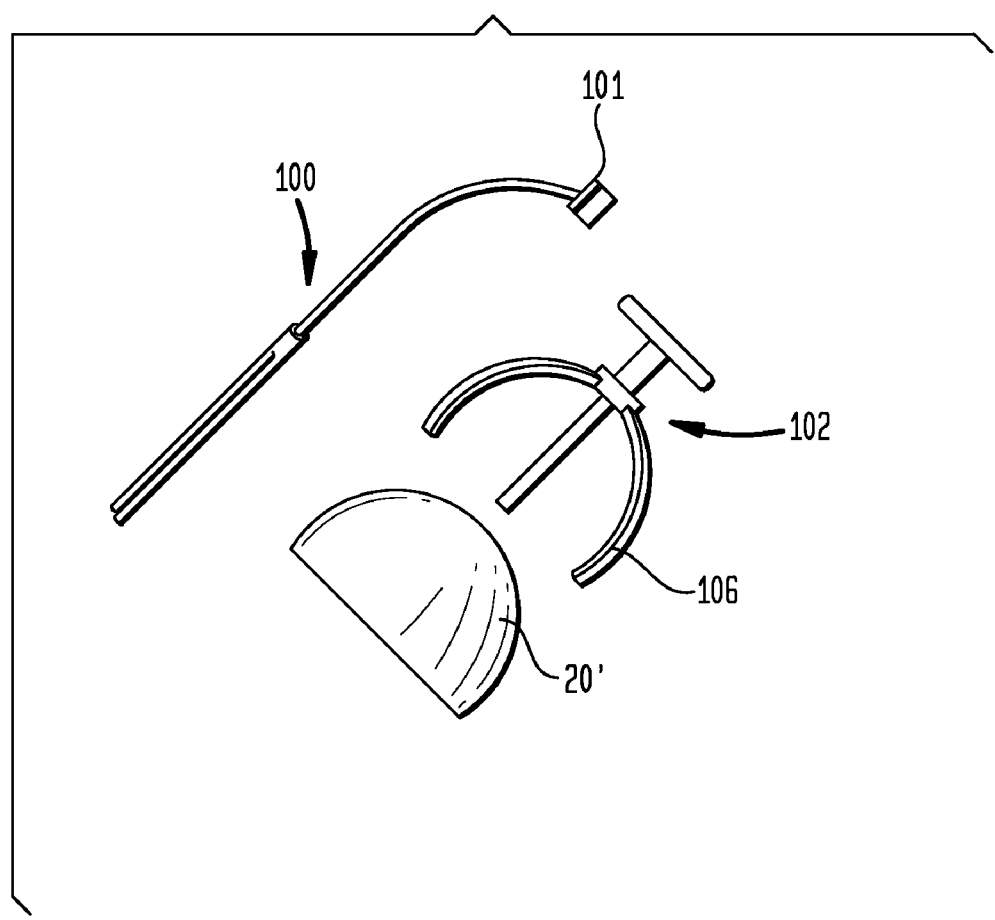
Figure 24:
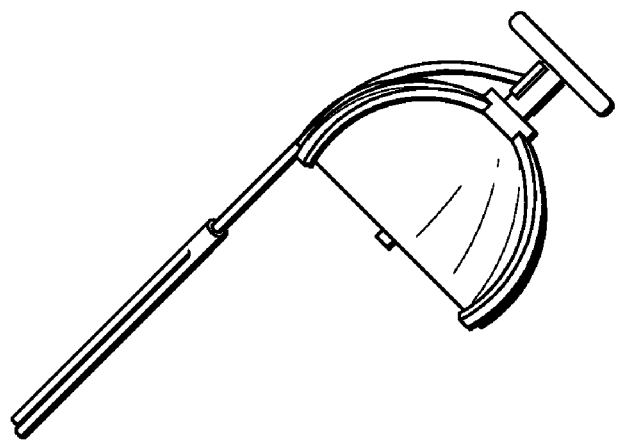

The prosthesis alignment jig 100, shown in FIGS. 23 and 24, is similar to the pin alignment jig 90 except that rather than having a cylindrical portion with a bore 92 mounted at the proximal end, a prosthesis holder 102 is mounted to a mount 101. The ball 20' is gripped by three retention prongs 106, that are connected to an interface body in a manner similar to that described in connection with the third embodiment. The ball 20' may be captured or released by deflecting the retention prongs 106, as shown, or by any of the methods discussed above in connection with the third embodiment.

Figure 25:
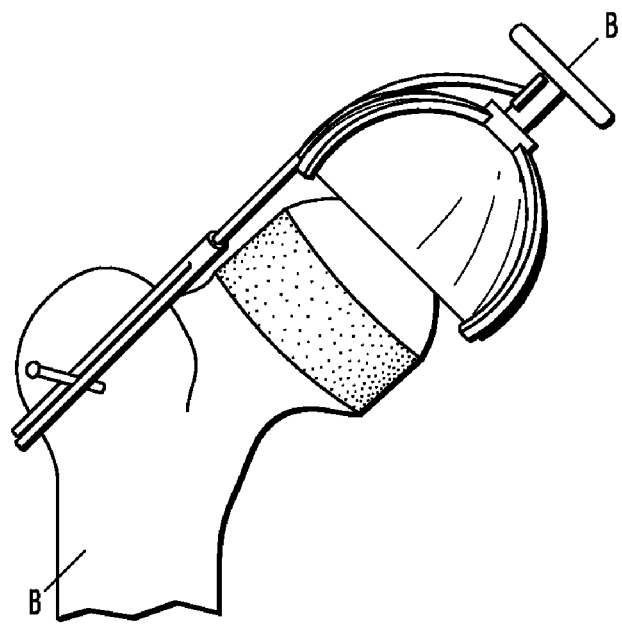
Figure 26:
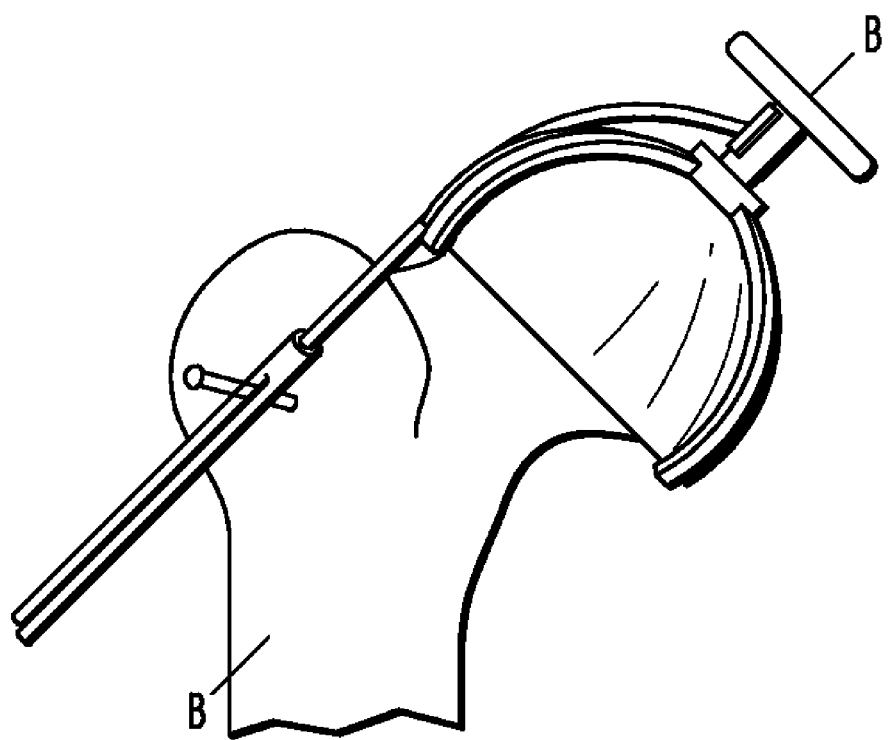

The prosthesis 20' is installed in the prosthesis alignment jig 100 and the jig 100 is aligned with the femoral head axis using the mount 94 on the side of the femur as shown in FIG. 25. The prosthesis alignment jig 100 is then used to install the prosthesis 10 in a manner similar to the third embodiment as shown in FIG. 26. Subsequently, the retention prongs 106 are released, the jig 100 is removed, and the pin 94 is removed.

It is noteworthy that the tools and methods of this aspect of the fourth embodiment, as described above, allow considerably more degrees of freedom, such as rotation about the pin 94, for the path of the jig 100 as the ball 20' is seated. It has been found that this simplified tooling is sufficient to seat the prosthesis and provide increased accuracy in the placement of the prosthesis because the axis of the pin 94 intersects the prepared femoral head axis B-B and the ball is sufficiently guided toward the head axis to prevent cocking and allow accurate placement of the prosthesis 20.

A person of skill in the art will appreciate that the tools and methods of the fourth embodiment can readily provide increased control of any of the degrees of translational or rotational freedom by various methods known in the art. For example, the pin 94 may have flats oriented parallel with the head axis B-B that slidingly engage with the slots of the fittings 96 of both the jigs 90 and 100 to prevent rotation about the pin axis and keep the jigs aligned with the head axis. As another example, a pair of stops may be fixed on the pin 94 at both sides of the fittings 96 to establish a radial datum that is transferred from the pin jig 90 to the prosthesis jig 100 to prevent the radial translation or rotation of the prosthesis jig relative to the pin.

It is also possible to combine the attributes of the third and fourth embodiment in a hybrid embodiment to provide control of additional degrees of freedom while retaining the relative simplicity of the fourth embodiment. For instance, the pin alignment jig 90 may be fitted with a joint such as multi-axial adjuster 88 configured to allow the pin 94 to be clamped by the collet 89 to lock the position of the jig in alignment with axis B-B. In this embodiment, the proximal portion of the alignment jig 90 has a fitting allowing the proximal portion to be detached and replaced with a second proximal portion having the features of the prosthesis jig 100 and allowing the prosthesis to translate only in the axis B-B.

The modular components of tools according to the embodiments of the invention described above are particularly well suited for inclusion in a kit that can be used by a surgeon to implant femoral ball components 20 and 20' of different sizes by providing the various prosthesis holders of the invention in various sizes corresponding to the prostheses sizes.

Unless stated to the contrary, any use of the words such as "including," "containing," "comprising," "having" and the like, means "including without limitation" and shall not be construed to limit any general statement that it follows to the specific or similar items or matters immediately following it.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of installing a femoral sleeve prosthesis to a femoral head comprising:

preparing an outer surface of the femoral head about a datum to a predetermined configuration to create a prepared femoral head having a head axis defined by the datum;

selecting a sleeve prosthesis having a distal end with an opening into a cavity and a proximal end having an aperture, the cavity being sized and configured to engage the outer surface of the prepared femoral head;

inserting the sleeve prosthesis into a sleeve interface of a tool and retaining the sleeve prosthesis in the sleeve interface, the tool further comprising a guide and a handle, the guide capable of aligning the sleeve interface with the head axis when engaged with the datum and guiding the sleeve interface to slidingly translate along the head axis when engaged with the datum, the handle capable of applying force to the interface portion;

engaging the guide of the tool with the datum;

applying force to the tool handle to slidingly translate the tool and sleeve prosthesis along the head axis to seat the sleeve cavity on the prepared femoral head surface; and releasing the sleeve prosthesis from the sleeve interface, disengaging the guide from the datum and removing the tool, wherein the datum is a guide wire bore, and the guide comprises a pin extending from the sleeve interface, the pin being configured to slidingly fit in the guide wire bore when the pin is engaged with the guide wire bore by passing the pin through the aperture and cavity of the sleeve prosthesis when inserting the sleeve prosthesis into the sleeve interface and then positioning the tool to place the pin into the guide wire bore.

2. The method of claim 1, wherein the sleeve prosthesis has at least one outer surface that is tapered.

3. The method of claim 2, wherein the sleeve prosthesis is released from the sleeve interface by actuating an extractor assembly that applies force to the sleeve prosthesis to release the sleeve prosthesis from the tool.

4. The method of claim 3, wherein the force applied by the extractor assembly is applied symmetrically about a central axis of the proximal end of the sleeve prosthesis.

5. The method of claim 2, wherein the sleeve interface has at least one surface that is partially cone shaped.

6. The method of claim 1, wherein bone cement is applied between an interior surface of the sleeve prosthesis and a surface of the prepared femoral head prior to seating the cavity of the sleeve prosthesis on the surface of the prepared femoral head.

7. The method of claim 1, wherein an outside surface of the sleeve prosthesis is solid metal.

8. The method of claim 1, wherein the sleeve prosthesis is substantially composed of one metal selected from the group consisting of titanium, titanium alloys, cobalt chrome alloys, niobium and tantalum.

* * * * *